(12) United States Patent
Park et al.

(10) Patent No.: US 8,012,607 B2
(45) Date of Patent: Sep. 6, 2011

(54) CYCLOPENTAPHENANTHRENE-BASED COMPOUND AND ORGANIC LIGHT EMITTING DEVICE EMPLOYING THE SAME

(75) Inventors: Sang-hoon Park, Yongin-si (KR); O-hyun Kwon, Yongin-si (KR)

(73) Assignees: Samsung Electronics Co., Ltd., Maetan-dong, Yeongtong-gu, Suwon-si, Gyeonggi-do (KR); Samsung Mobile Display Co., Ltd., Nongseo-Dong, Giheung-Gu, Yongin, Gyunggi-Do (KR)

( * ) Notice: Subject to any disclaimer, the term of this patent is extended or adjusted under 35 U.S.C. 154(b) by 627 days.

(21) Appl. No.: 12/073,549

(22) Filed: Mar. 6, 2008

(65) Prior Publication Data

US 2009/0117404 A1    May 7, 2009

(30) Foreign Application Priority Data

Nov. 5, 2007 (KR) .................. 10-2007-0112304

(51) Int. Cl.
*H01L 51/54* (2006.01)
*C09K 11/06* (2006.01)
*C07C 211/00* (2006.01)

(52) U.S. Cl. .................. 428/690; 564/426; 564/429

(58) Field of Classification Search .................. 428/690, 428/917; 564/426–429, 434; 313/504, 506; 257/40, E51.051
See application file for complete search history.

(56) References Cited

U.S. PATENT DOCUMENTS

| 4,885,211 A | 12/1989 | Tang et al. |
| 5,151,629 A | 9/1992 | VanSlyke |
| 2005/0158583 A1 * | 7/2005 | Kim et al. .................. 428/690 |

FOREIGN PATENT DOCUMENTS

JP    05-234681    9/1993

* cited by examiner

*Primary Examiner* — Angela Ortiz
*Assistant Examiner* — J. L. Yang
(74) *Attorney, Agent, or Firm* — Robert E. Bushnell, Esq.

(57) ABSTRACT

Provided are a cyclopentaphenanthrene-based compound represented by Formula 1 below and an organic light emitting device employing the same.

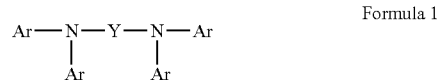

Formula 1

Here, Y and Ar are described in the detailed description.

9 Claims, 2 Drawing Sheets

CYCLOPENTAPHENANTHRENE-BASED COMPOUND AND ORGANIC LIGHT EMITTING DEVICE EMPLOYING THE SAME

CLAIM OF PRIORITY

This application makes reference to, incorporates the same herein, and claims all benefits accruing under 35 U.S.C. §119 from an application for earlier filed in the Korean Intellectual Property Office on Nov. 5, 2007 and there duly assigned Serial No. 10-2007-0112304.

BACKGROUND OF THE INVENTION

1. Field of the Invention

The present invention relates to a cyclopentaphenanthrene-based compound and an organic light emitting device employing the same, and more particularly, to an aromatic amine compound including cyclopentaphenanthrene and an organic light emitting device including an organic layer having the same.

2. Description of the Related Art

Organic light emitting devices are active light emitting display devices that emit light by recombination of electrons and holes in a thin layer made of a fluorescent or phosphorescent organic compound (an organic layer) when a current is applied to the organic layer. The organic light emitting devices have advantages such as lightweight, simple constitutional elements, easy fabrication process, superior image quality and wide viewing angle. Furthermore, the organic light emitting devices can accomplish perfect creation of dynamic images and high color purity. The organic light emitting devices also have electrical properties suitable for portable electronic equipment such as low power consumption and low driving voltage.

A multi-layered organic light emitting device using an aluminum quinolinol complex layer and a triphenylamine derivative layer was developed by Eastman Kodak Co. (U.S. Pat. No. 4,885,211), and a wide range of light from ultraviolet lights to infrared lights can be emitted using low-molecular weight materials when an organic emitting layer is formed (U.S. Pat. No. 5,151,629).

Light emitting devices, which are self light emitting display devices, have wide viewing angles, excellent contrast and quick response. Light emitting devices are classified into inorganic light emitting devices using inorganic compounds to form emitting layers and organic light emitting devices (OLED) using organic compounds to form emitting layers. Organic light emitting devices have higher brightness, lower driving voltages and quicker responses than inorganic light emitting devices and can realize multi colors. Thus, organic light emitting devices have been actively studied.

Typically, an organic light emitting device has an anode/organic emitting layer/cathode structure. An organic light emitting device can also have various other structures, such as an anode/hole injection layer/hole transport layer/emitting layer/electron transport layer/electron injection layer/cathode structure or an anode/hole injection layer/hole transport layer/emitting layer/hole blocking layer/electron transport layer/electron injection layer/cathode structure.

Materials that are used in organic light emitting devices can be classified into vacuum deposited materials and solution coated materials according to a method of preparing an organic layer. The vacuum deposited materials may have a vapor pressure of $10^{-6}$ torr or greater at the temperature of 500° C. or less and be low molecular materials having a molecular weight of 1200 or less. The solution coated materials may be highly soluble in solvents to be prepared in solution phase, and include aromatic or heterocyclic groups.

When an organic light emitting device is manufactured by vacuum deposition, costs may be increased due to expensive vacuum systems and high resolution pixels may not be easily manufactured if a shadow mask is used to prepare pixels for a natural color display. On the other hand, an organic light emitting device can be easily and inexpensively manufactured using solution coating such as inkjet printing, screen printing and spin coating and can have relatively high resolution compared to when using a shadow mask.

Meanwhile, when an organic light emitting device is operated or stored at a high temperature, emitting light may be changed, light emitting efficiency may be reduced, driving voltages may be increased, and lifetime may be shortened. In order to prevent those problems, a glass transition temperature (Tg) of hole injecting materials, hole transporting materials and emitting materials. In order to have high Tg, molecules of the materials have many aromatic groups which cause crystallization of the molecules 11 during the formation of a thin film and the crystallization may cause defects in the thin film. Meanwhile, the high Tg increases sumlimation temperature and the lifetime of organic light emitting devices may be decreased due to decomposition of materials during deposition or ununiform deposition.

Japanese Patent Publication No. hei 5-234681 discloses N,N-diphenyl-N,N-di(1-naphtyl)-1,1-biphenyl-4,4-diamine (NPD) having a higher Tg than N,N-diphenyl-N,N-dimethylphenyl-1,1-biphenyl-4,4-diamine (TPD) which has been commonly used in the art as a hole transporting material to improve thermal stability by introducing a condensed aromatic ring into a molecule.

SUMMARY OF THE INVENTION

According to an aspect of the present invention, there is provided a cyclopentaphenanthrene-based compound represented by Formula 1 below:

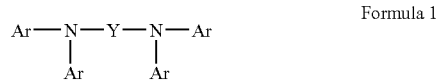

Formula 1 wherein Y is a bivalent linking group and selected from the group consisting of a substituted or unsubstituted C6-C30 arylene group or a substituted or unsubstituted C2-C30 heteroarylene group;

at least one of Ars is a substituent represented by Formula 2, and the others which are identical to or different from each other are a substituted or unsubstituted C6-C30 aryl group:

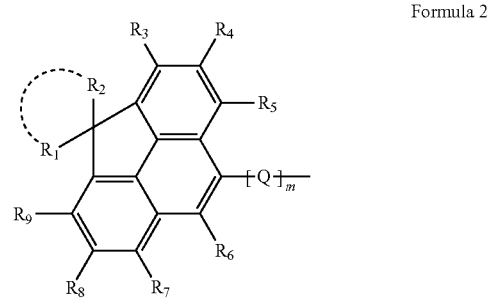

Formula 2 wherein $R_1$ and $R_2$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group; or $R_1$ and $R_2$ are linked to form one selected from the group consisting of a substituted or unsubstituted C3-C20 aliphatic ring, a substituted or unsubstituted C5-C30 heteroaliphatic ring, a substituted or unsubstituted C6-C30 aromatic ring and a substituted or unsubstituted C2-C30 heteroaromatic ring;

$R_3$ to $R_9$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

m is 1, 2 or 3; and

Q is a bivalent group represented by one of the formulae below:

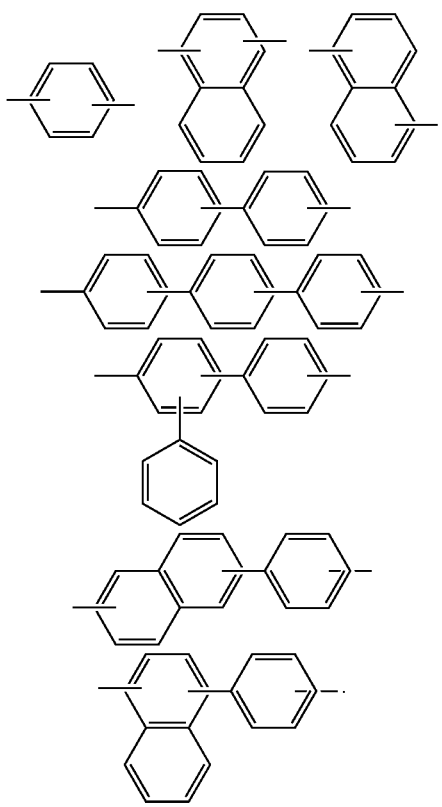

According to another aspect of the present invention, there is provided an organic light emitting device comprising:
a first electrode;
a second electrode; and
at least one organic layer between the first electrode and the second electrode, wherein the organic layer comprises the cyclopentaphenanthrene-based compound.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
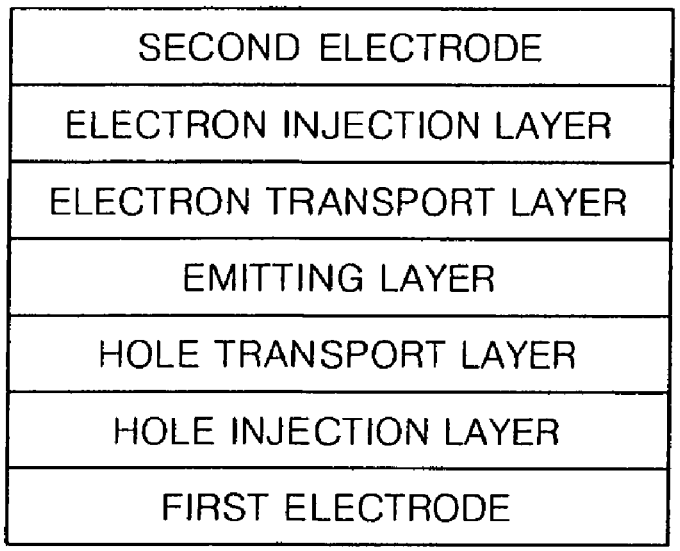
FIG. 1A is a schematic sectional view of an organic light emitting device according to an embodiment of the present invention.

Hereinafter, the present invention will now be described more fully with reference to the accompanying drawings, in which exemplary embodiments of the invention are shown.

An aromatic amine compound including cyclopentaphenanthrene according to an embodiment of the present invention is represented by Formula 1 below.

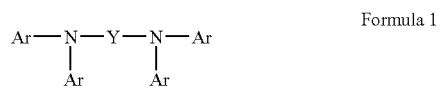

Formula 1

Here, Y, as a bivalent linking group, is a substituted or unsubstituted C6-C30 arylene group or a substituted or unsubstituted C2-C30 heteroarylene group;

at least one of Ars is a substituent represented by Formula 2, and the others are a substituted or unsubstituted C6-C30 aryl group:

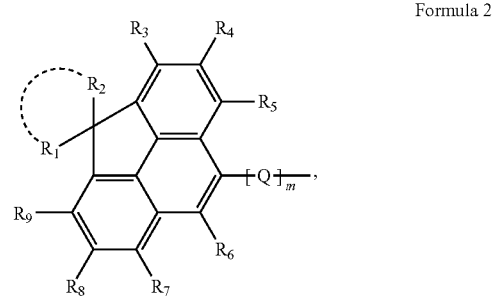

Formula 2 wherein m is 1, 2 or 3.

The compound according to an embodiment of the present invention includes at least one cyclopentaphenanthrene having a rigid structure as shown in Formula 2. Meanwhile, in the compound according to the present invention, cyclopentaphenanthrene is connected to a nitrogen atom of an amino group via the C8 position of the cyclopentaphenanthrene. Here, cyclopentaphenanthrene may be connected to the nitrogen atom via a bivalent linking group Q as shown in Formula 2, and the bivalent linking group Q may be any one of the compounds represented by formulae below.

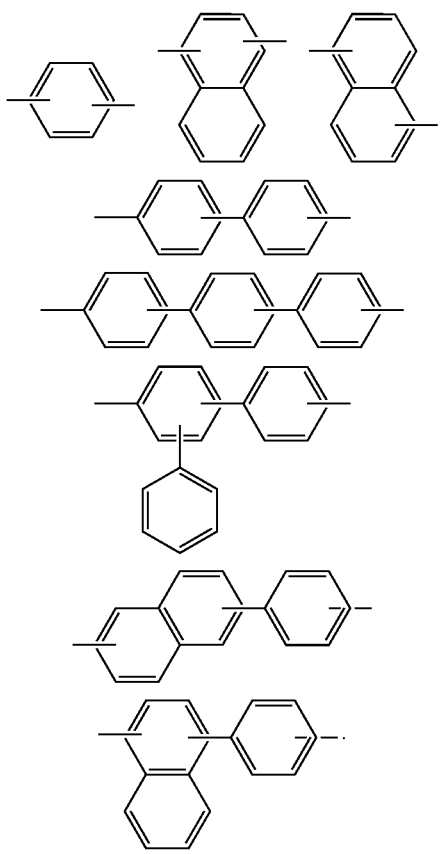

At least one hydrogen atom of the aryl group of the cyclopentaphenanthrene may be, each independently, substituted with a halogen group, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group or a substituted or unsubstituted C2-C30 heteroaryl group.

Various substituents may be easily introduced into the C4 position of cyclopentaphenanthrene. That is, two hydrogen atoms at the C4 position of the cyclopentaphenanthrene may be each independently a halogen group, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group or a substituted or unsubstituted C2-C30 heteroaryl group.

Meanwhile, in Formula 2, $R_1$ and $R_2$ of the C4 position of the cyclopentaphenanthrene may be linked to form a ring which may be selected from the group consisting of a substituted or unsubstituted C3-C20 aliphatic ring, a substituted or unsubstituted C5-C30 heteroaliphatic ring, a substituted or unsubstituted C6-C30 aromatic ring and a substituted or unsubstituted C2-C30 heteroaromatic ring. When the $R_1$ and $R_2$ are linked to form a ring, the compound of Formula 2 may have one of the structures shown below.

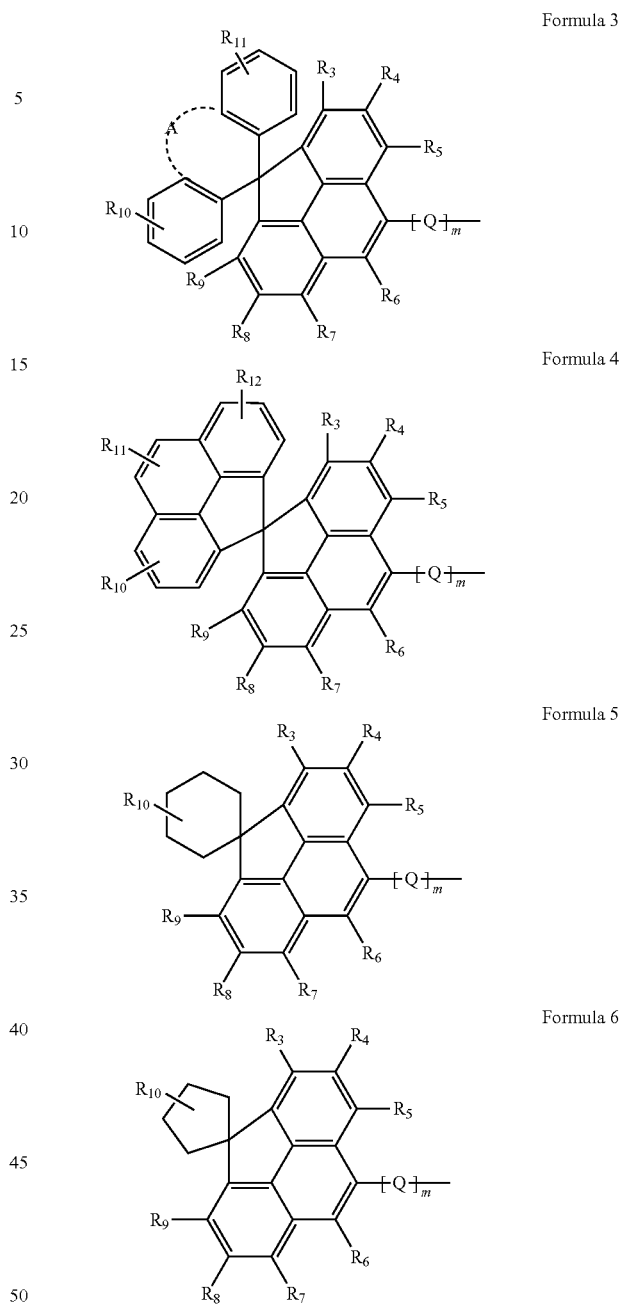

Here, $R_{10}$ to $R_{12}$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group; and A is an oxygen atom, a sulfur atom, or a C1-C5 alkylene group ($-(CH_2)_p-$), wherein p is an integer of 1 to 5, and preferably A is a C1-C2 alkylene group; and $R_3$ to $R_9$, Q and m are described above with respect to Formula 1.

In Formula 1, two nitrogen atoms are connected to each other by Y which is a bivalent linking group selected from the group consisting of a substituted or unsubstituted C6-C30 arylene group and a substituted or unsubstituted C2-C30 heteroarylene group, and Y is represented by any one of the formulae below:

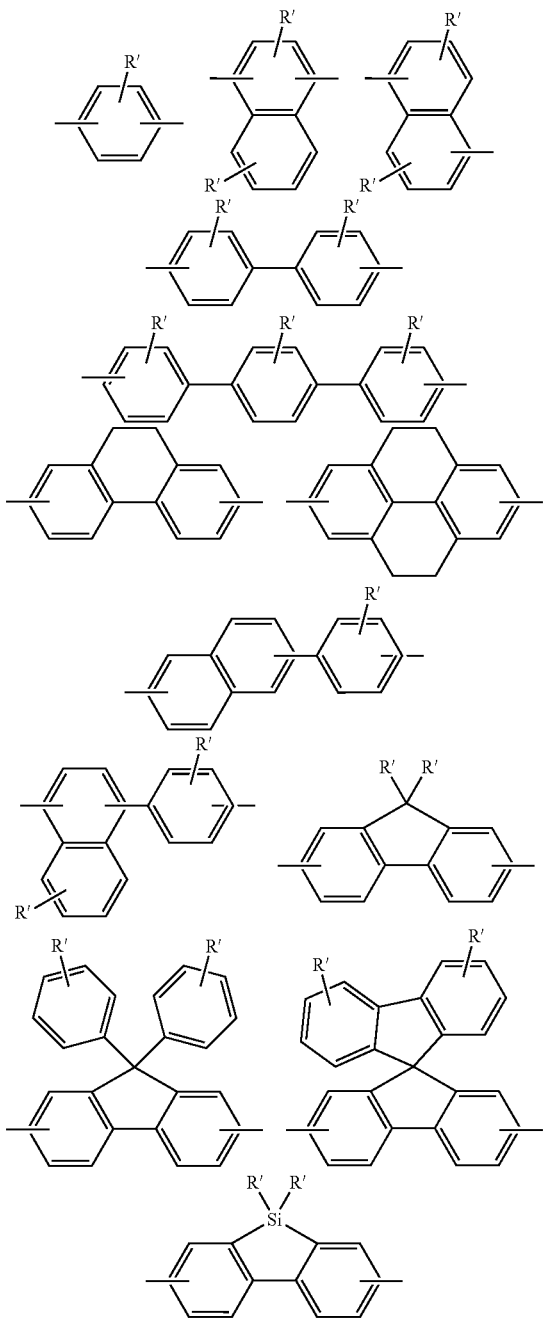

wherein R' is a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group or a substituted or unsubstituted C1-C20 alkoxy group.

The compound of Formula 2 may be one of the compounds represented by Formulae 7 to 9 below:

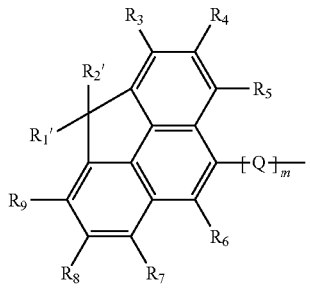

Formula 7

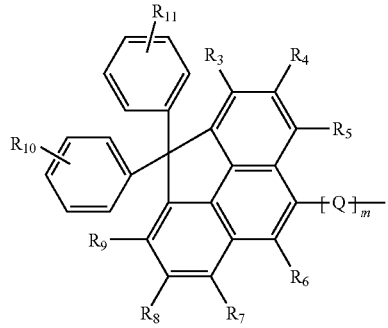

Formula 8

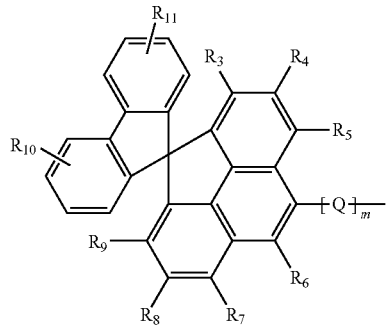

Formula 9 wherein $R_1'$, $R_2'$, $R_{10}$ and $R_{11}$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group; and $R_3$ to $R_8$, Q and m are described above with respect to Formula 1.

In Formula 1, Ar which is not represented by Formula 2 may be a substituted or unsubstituted C6-C30 aryl group, and preferably represented by any one of the formulae below.

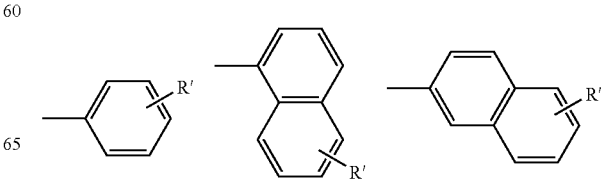

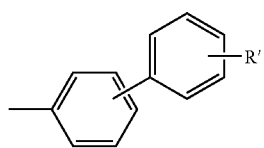
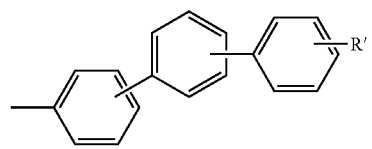
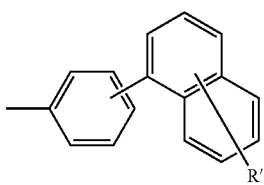
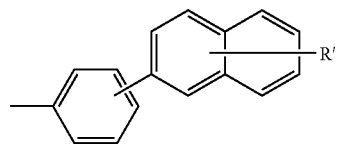
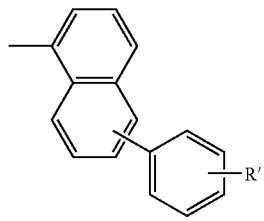
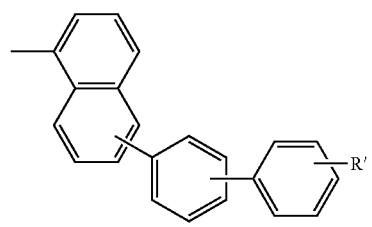
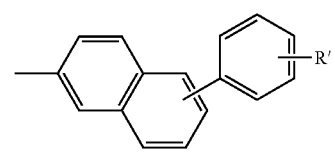
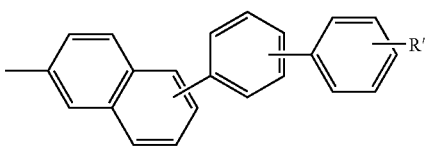
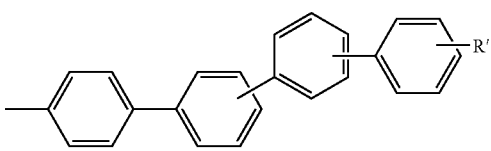
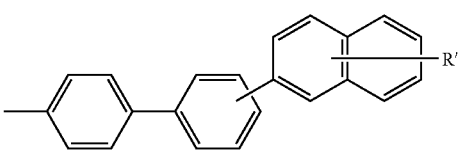
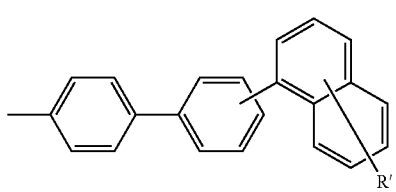
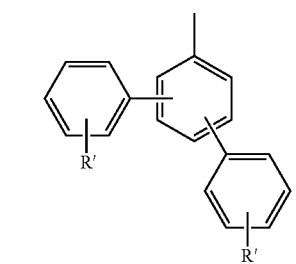
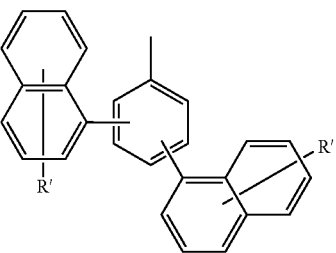
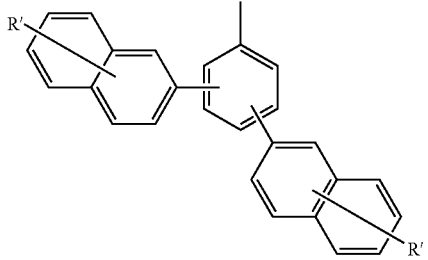

Here, R' is selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group and a substituted or unsubstituted C1-C20 alkoxy group.

The alkyl group used herein as a substituent may be a linear or branched alkyl group having 1 to 20 carbon atoms, preferably 1 to 12 carbon atoms, and more preferably 1 to 6 carbon atoms. Examples of the unsubstituted alkyl group are a methyl group, an ethyl group, an n-propyl group, an isopropyl group, a n-butyl group, an isobutyl group, a sec-butyl group, a t-butyl group, a pentyl group, an iso-amyl group and a hexyl group.

The cycloalkyl group used herein is a monovalent monocyclic system having 3 to 20 carbon atoms, preferably 3 to 10 carbon atoms, and more preferably 3 to 6 carbon atoms.

The heterocycloalkyl group used herein is a monovalent monocyclic system having 3 to 20 carbon atoms, preferably 3 to 10 carbon atoms, and more preferably 3 to 6 carbon atoms and 1, 2 or 3 hetero atoms selected from the group consisting of N, O, P and S.

The alkoxy group used herein may be an oxygen-containing linear or branched alkoxy group having alkyl moiety consisting of 1 to 20 carbon atoms, preferably 1 to 6 carbon atoms, and more preferably 1 to 3 carbon atoms. Examples of the alkoxy group are a methoxy group, an ethoxy group, a propoxy group, a butoxy group and a t-butoxy group. Such an alkoxy group can further be substituted by at least one halo atom such as fluoro, chloro and bromo to provide a haloalkoxy group. Examples of the haloalkoxy group are a fluoromethoxy group, a chloromethoxy group, a trifluoromethoxy group, a trifluoroethoxy group, a fluoroethoxy group and a fluoropropoxy group.

The aryl group as a substituent is used alone or in a combination, and is a carbocyclic aromatic system having 6 to 30 carbon atoms and one or more rings. The rings may be attached or fused together using a pendent method. The term "aryl" includes aromatic radicals such as phenyl, naphthyl, tetrahydronaphthyl, indane and biphenyl. For example, the aryl group may be phenyl.

The aralkyl used herein is an alkyl group in which at leas one hydrogen atom is substituted with the aryl group.

The heteroaryl group used herein as a substituent is a monovalent monocyclic or bicyclic aromatic radical that includes 1, 2 or 3 hetero atoms selected from N, O or S and includes a ring composed of 5 to 30 carbon atoms. The heteroaryl group may be a monovalent monocyclic or bicyclic aromatic radical in which the hetero atoms is oxidized or quaternarized to form, for example, an N-oxide or a quaternary salt. Examples of the heteroaryl group are thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrolyl, indolyl, 2-pyridonyl, N-alkyl-2-pyridonyl, pyrazinonyl, pyridazynonyl, pyrimidinonyl, oxazolonyl, corresponding N-oxides thereof (e.g., pyridyl N-oxide and quinolinyl N-oxide), and quaternary salts thereof, but are not limited thereto.

When the alkyl group, the alkoxy group, the aryl group, the heteroaryl group, the cycloalkyl group and the heterocloalkyl group are substituted, the substituents may be at least one of —F; —Cl; —Br; —CN; —NO$_2$; —OH; a C1-C20 alkyl group that is unsubstituted or substituted with —F, —Cl, —Br, —CN, —NO$_2$ or —OH; a C1-C20 alkoxy group that is unsubstituted or substituted with —F, —Cl, —Br, —CN, —NO$_2$ or —OH; a C6-C30 aryl group that is unsubstituted or substituted with a C1-C20 alkyl group, a C1-C20 alkoxy group, —F, —Cl, —Br, —CN, —NO$_2$ or —OH; a C2-C30 heteroaryl group that is unsubstituted or substituted with a C1-C20 alkyl group, a C1-C20 alkoxy group, —F, —Cl, —Br, —CN, —NO$_2$ or —OH; a C5-C20 cycloalkyl group that is unsubstituted or substituted with a C1-C20 alkyl group, a C1-C20 alkoxy group, —F, —Cl, —Br, —CN, —NO$_2$ or —OH; a C5-C30 heterocycloalkyl group that is unsubstituted or substituted with a C1-C20 alkyl group, a C1-C20 alkoxy group, —F, —Cl, —Br, —CN, —NO$_2$ or —OH; and —N(G6)(G7). Here, G6 and G7 are each independently a hydrogen atom; C1-C10 alkyl group; or a C6-C30 aryl group substituted with a C1-C10 alkyl group.

In more particular, $R_1$ to $R_{12}$ are each independently selected from the group consisting of a hydrogen atom, a halogen atom, a cyano group, a hydroxyl group, a C1-C10 alkyl group, a C1-C10 alkoxy group and a substituted or unsubstituted derivative as follows: a phenyl group, a biphenyl group, a pentalenyl group, an indenyl group, a naphthyl group, a biphenylenyl group, an anthracenyl group, an azulenyl group, a heptalenyl group, an acenaphtylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a fluorenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxyranyl group, a pyrrolidinyl group, a pyrazolidinyl group, an imidazolidinyl group, a piperidinyl group, a piperazinyl group, a morpholinyl group, a di(C6-C30 aryl)amino group, a tri(C6-C30 aryl) silyl group and derivatives thereof.

Here, the term "derivative" indicates the above-listed group in which at least one of the hydrogen atoms is substituted with the substituents described above.

The cyclopentaphenanthrene-based compound represented by Formula 1 according to an embodiment of the present invention has high solubility in a solvent in the formation of an organic layer, high thermal stability and excellent charge transporting capability.

The compound according to an embodiment of the present invention may be represented by one of Formulae 10 to 40 below, but is not limited thereto.

Formula 10
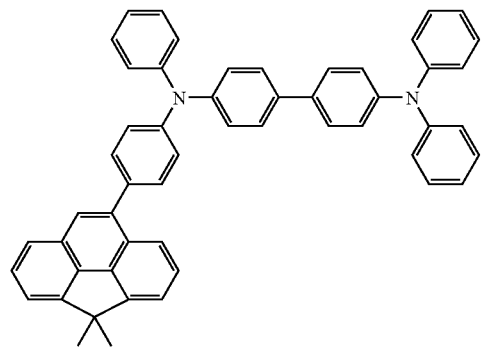
Formula 11
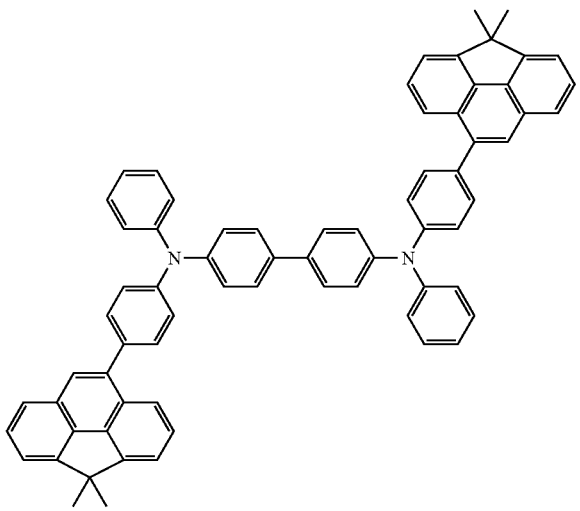
Formula 12
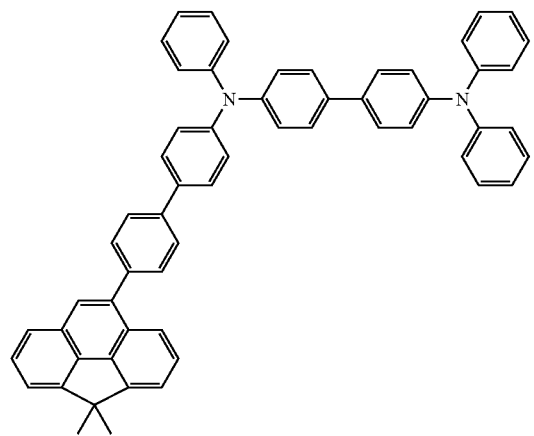
Formula 13
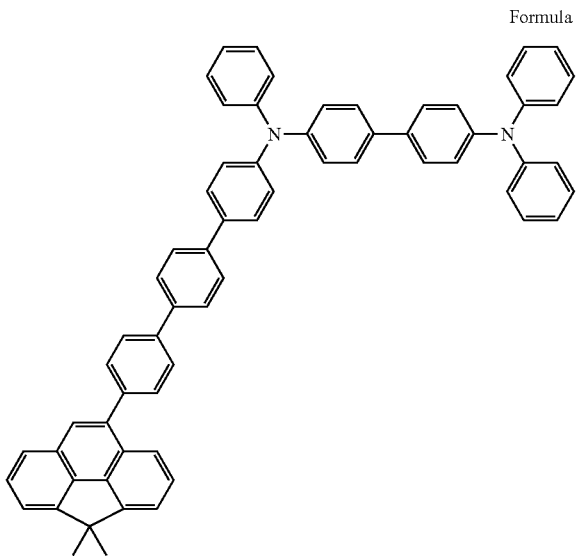
Formula 14
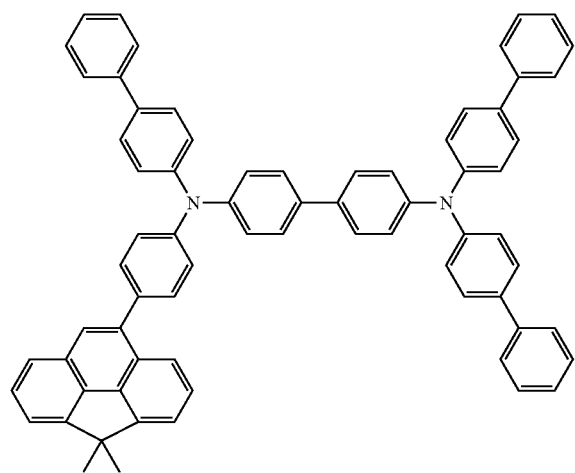
Formula 15
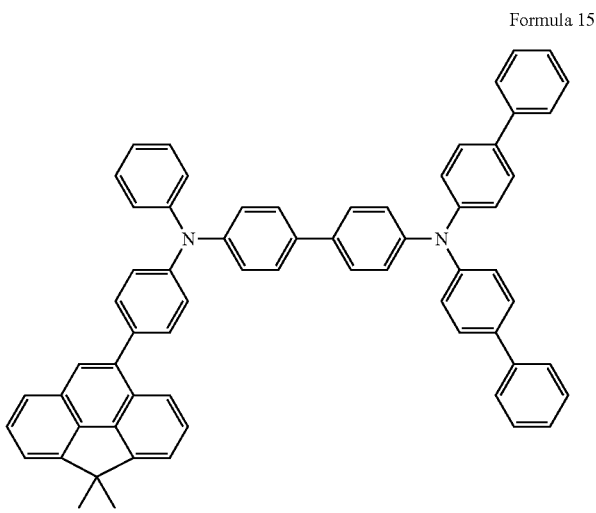

-continued
Formula 16
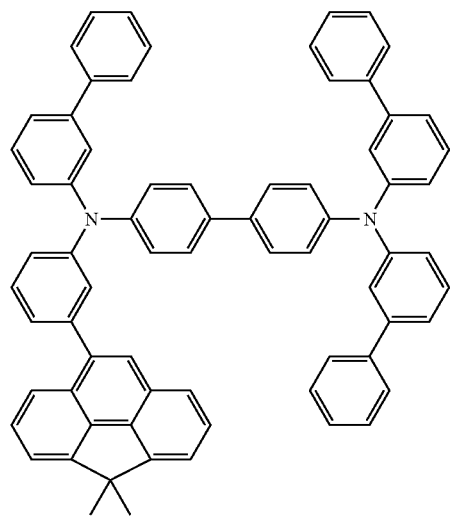
Formula 17
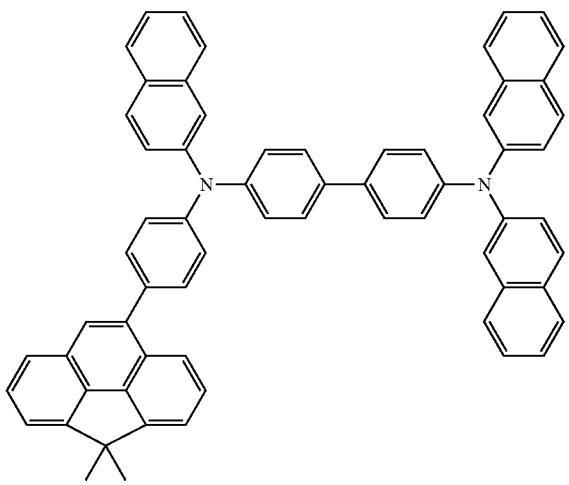
Formula 18
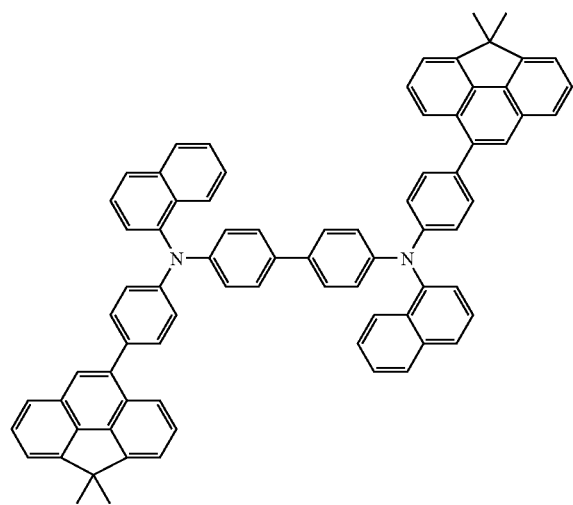
Formula 19
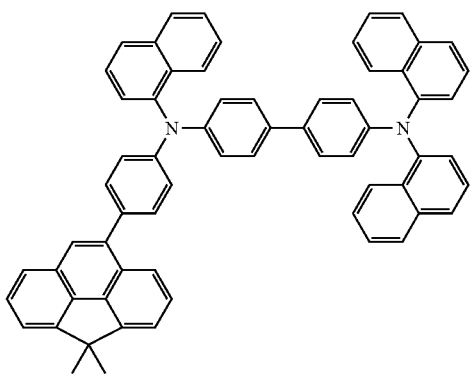
Formula 20
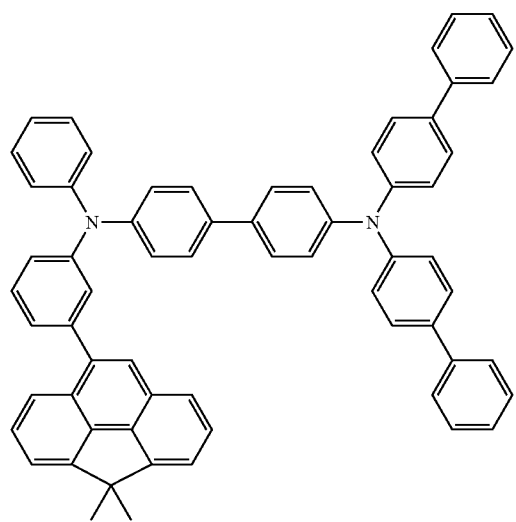
Formula 21
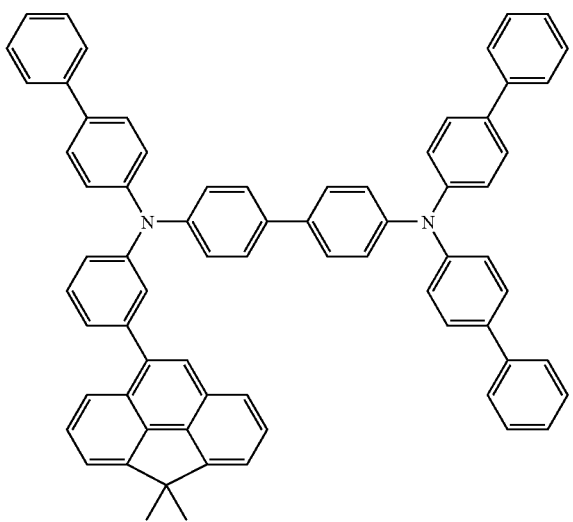

-continued
Formula 22
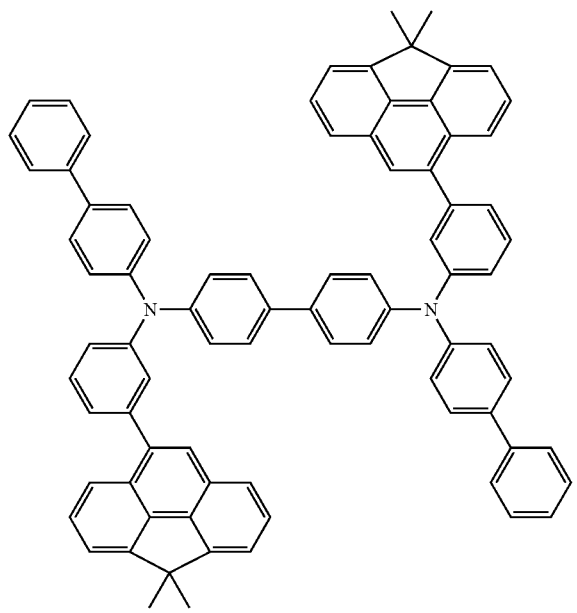
Formula 23
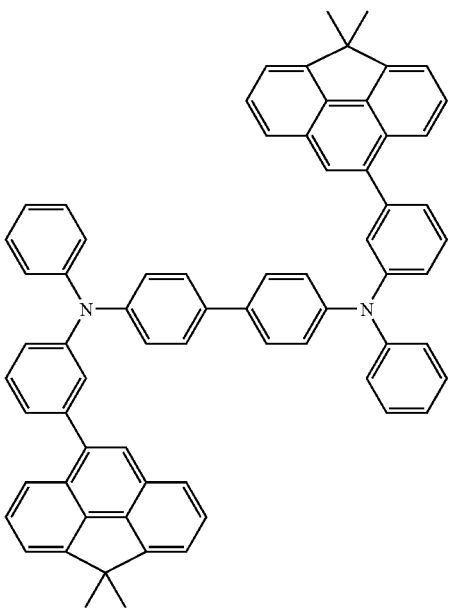
Formula 24
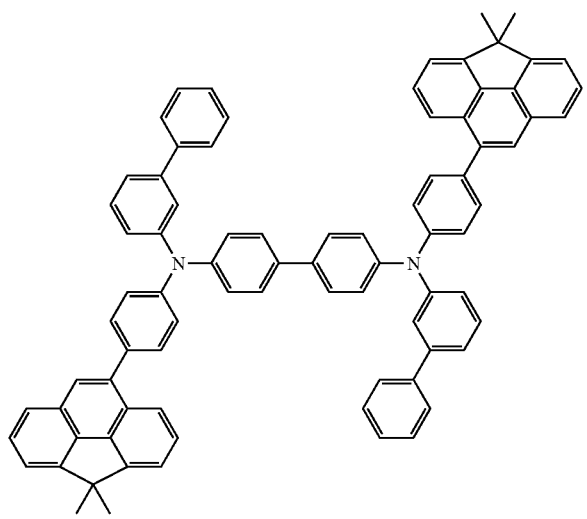
Formula 25
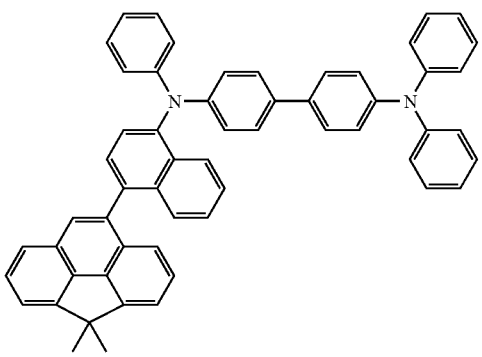
Formula 26
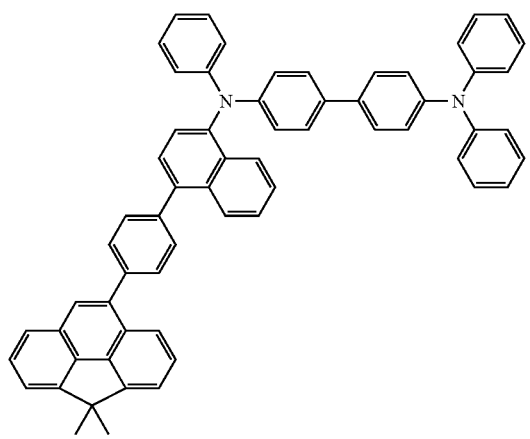
Formula 27
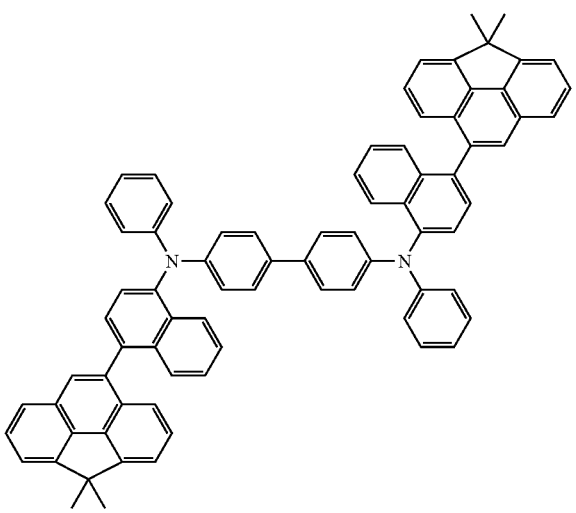

Formula 28
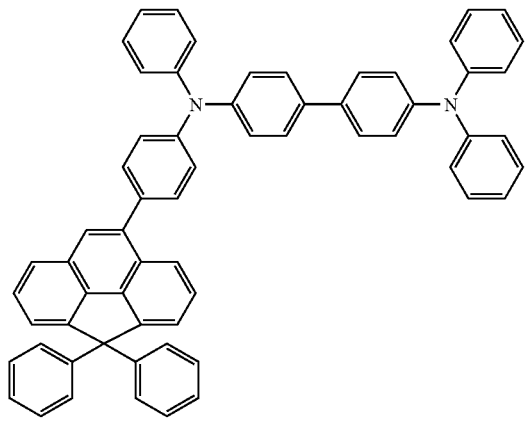
Formula 29
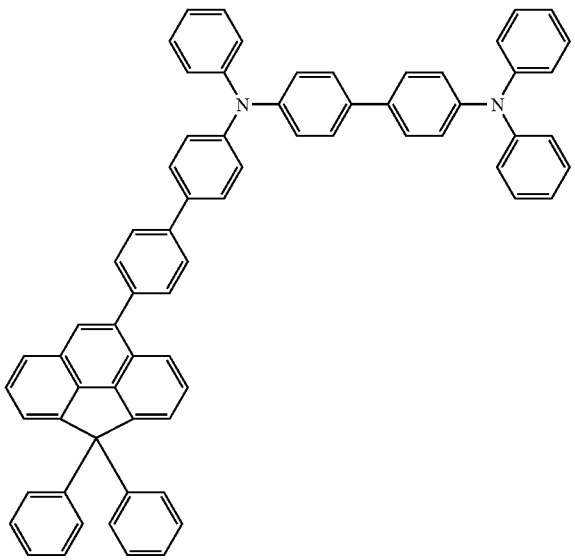
Formula 30
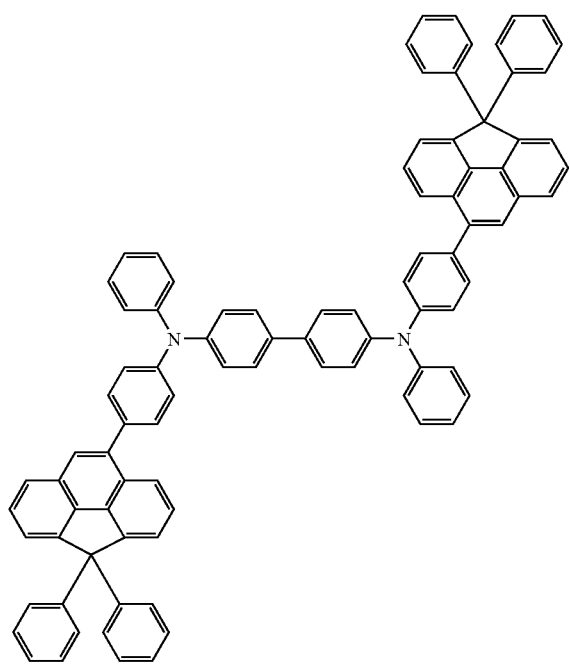
Formula 31
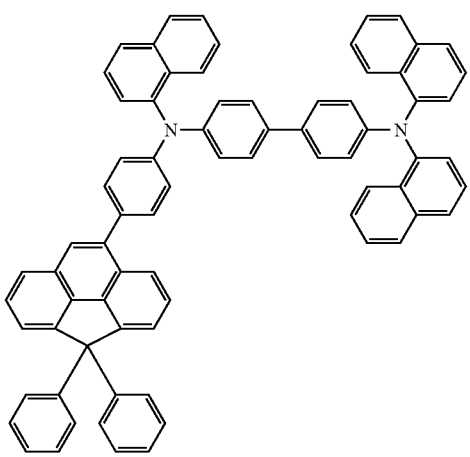

-continued
Formula 32
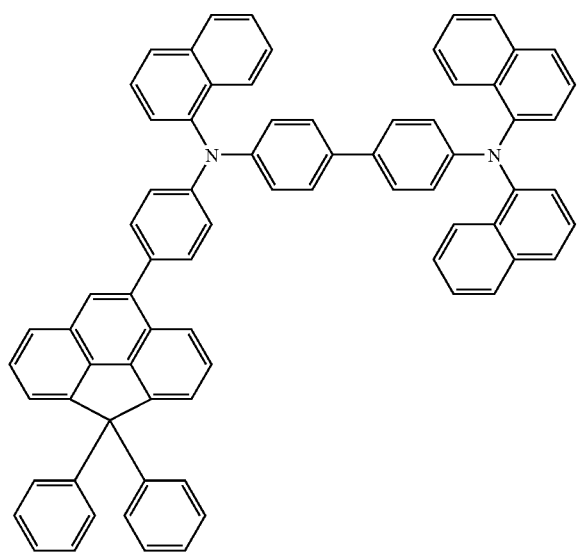
Formula 33
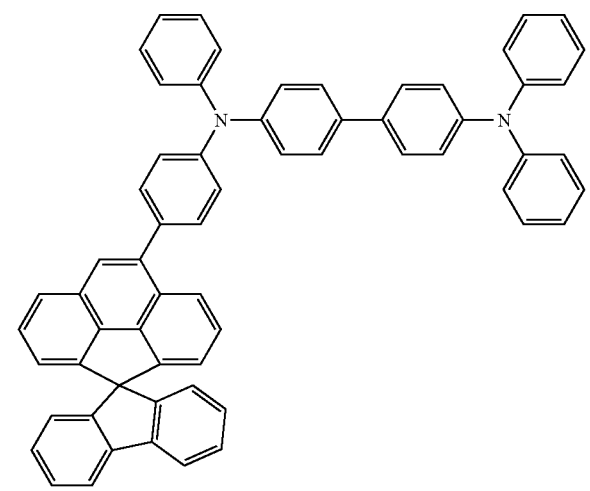
Formula 34
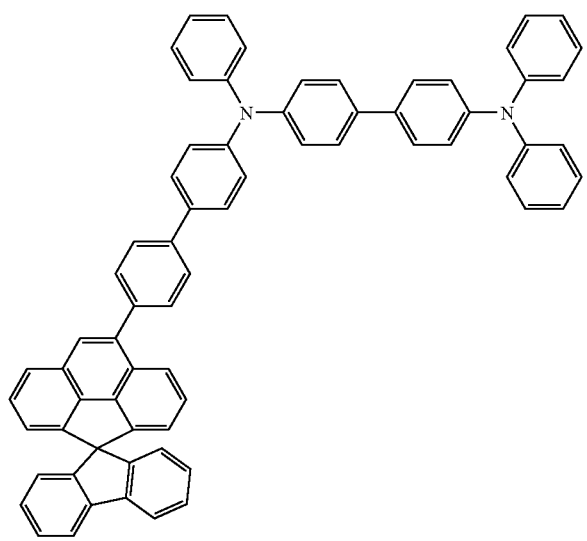
Formula 35
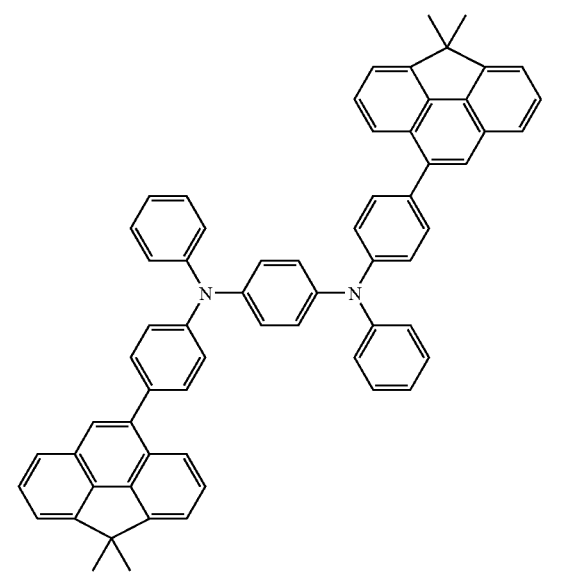
Formula 36
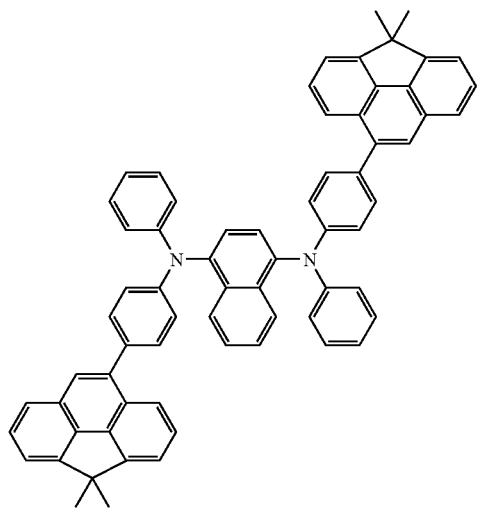
Formula 37
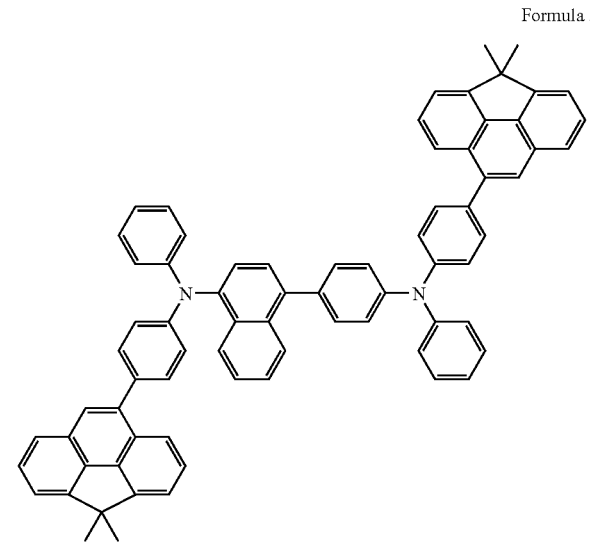

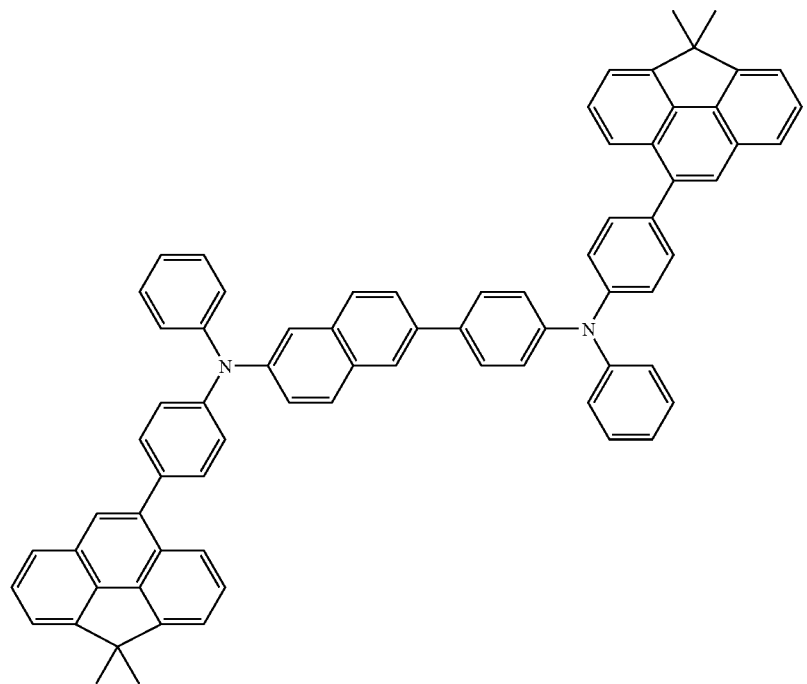
Formula 38
Formula 39

-continued

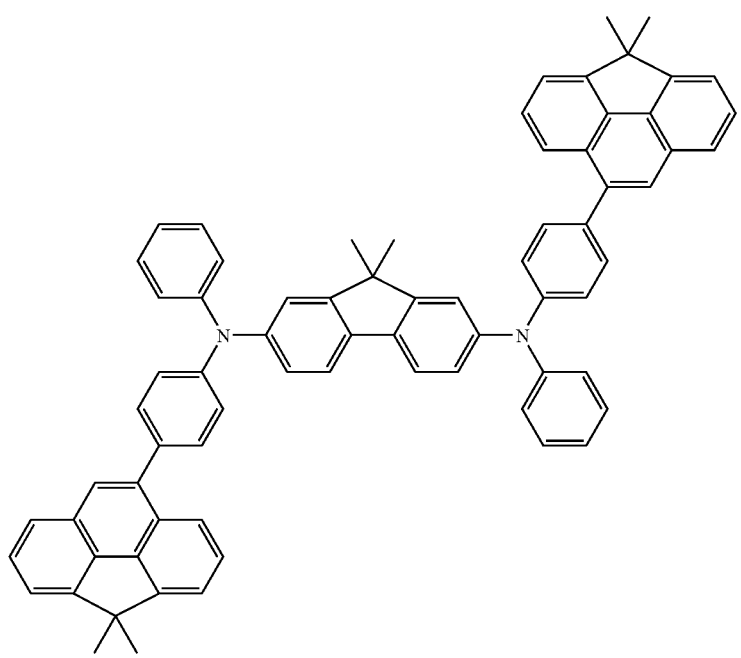

Formula 40

The compound of represented by Formula 1 according to an embodiment of the present invention may be synthesized using a method that is commonly used in the art. A synthetic pathway of the compound is described with respect to synthesis examples and examples.

An organic light emitting device according to an embodiment of the present invention includes a first electrode; a second electrode; and an organic layer interposed between the first electrode and the second electrode, wherein the organic layer includes at least one compound represented by Formula 1.

The compound of Formula 1 is suitably used to form an organic layer, preferably an emitting layer, a hole injection layer or a hole transport layer, and more preferably a hole transport layer.

The organic light emitting device of the present invention has improved emitting characteristics such as low driving voltage and high color purity by employing a compound having high solubility and thermal stability and capable of forming a stable organic layer when compared to a conventional organic light emitting device prepared using a solution coating method and having low stability of organic layer.

The organic light emitting device of the present invention may have various structures. That is, the organic light emitting device may further include at least one layer selected from the group consisting of a hole injection layer, a hole transport layer, a hole blocking layer, an electron blocking layer, an electron transport layer and an electron injection layer between the first electrode and the second electrode.

Figure 1B:
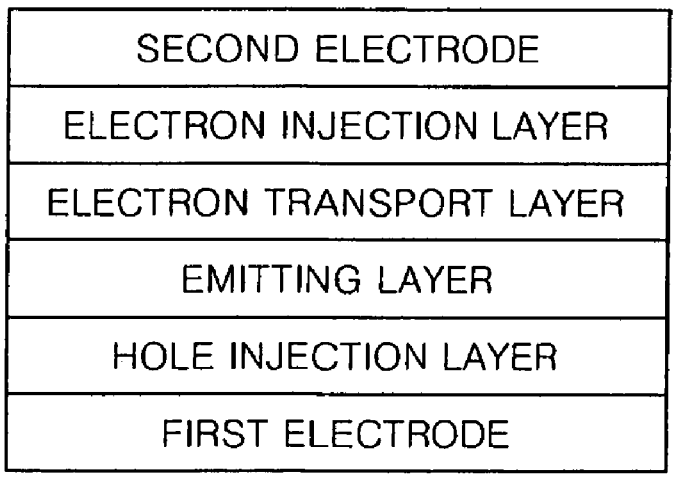
FIG. 1B is a schematic sectional view of an organic light emitting device according to another embodiment of the present invention.

More particularly, FIGS. 1A and 1B are schematic sectional views of organic light emitting devices according to embodiments of the present invention. The organic light emitting device of FIG. 1A has a structure of a first electrode/a hole injection layer/a hole transport layer/an emitting layer/an electron transport layer/an electron injection layer/a second electrode. The organic light emitting device of FIG. 1B has a structure of a first electrode/a hole injection layer/an emitting layer/an electron transport layer/an electron injection layer/a second electrode. An emitting layer of the organic light emitting device of the present invention may include a phosphorescent or fluorescent dopant for red, green, blue or white color. The phosphorescent dopant may be an organic metal compound including at least one element selected from the group consisting of Ir, Pt, Os, Ti, Zr, Hf, Eu, Tb and Tm.

Hereinafter, a method of preparing an organic light emitting device according to the present invention will be described with reference to FIG. 1A.

First, a first electrode is formed on a substrate, for example, by depositing or sputtering a high work-function material. The first electrode can be an anode. The substrate, which can be any substrate that is used in conventional organic light emitting devices, may be a glass substrate or a transparent plastic substrate with excellent mechanical strength, thermal stability, transparency, surface smoothness, ease of treatment, and waterproof. The material that is used to form the first electrode can be ITO, IZO, $SnO_2$, ZnO, or any transparent material which has high conductivity.

Then, a hole injection layer (HIL) can be formed on the first electrode by vacuum deposition, spin coating, casting, langmuir Blodgett (LB), or the like.

When the hole injection layer is formed by vacuum deposition, deposition conditions may vary according to a compound that is used to form the hole injection layer, and the structure and thermal properties of the hole injection layer to be formed. In general, however, conditions for vacuum deposition may include a deposition temperature of 100 to 500° C, a pressure of $10^{-8}$ torr to $10^{-3}$ torr, a deposition speed of 0.01 to 100 Å/sec, and a layer thickness of 10 Å to 5 µm.

When the hole injection layer is formed by spin coating, coating conditions may vary according to a compound that is used to form the hole injection layer, and the structure and thermal properties of the hole injection layer to be formed. In general, however, conditions for spin coating may include a coating speed of 2000 to 5000 rpm and a heat-treatment temperature of about 80 to 200° C. to remove a solvent after coating.

The compound of Formula 1 may be used to form the HIL. The thickness of the HIL may be in the range of about 100 to 10000 Å, and preferably in the range of 100 to 1000 Å. When the thickness of the HIL is less than 100 Å, the hole injecting ability of the HIL may be reduced. On the other hand, when the thickness of the HIL is greater than 10000 Å, a driving voltage of the device may be increased.

Then, a hole transport layer (HTL) can be formed on the HIL by vacuum deposition, spin coating, casting, LB, or the like. When the HTL is formed by vacuum deposition or spin coating, the conditions for deposition and coating are similar to those for the formation of the HIL, although conditions for the deposition and coating may vary according to the material that is used to form the HTL.

The compound of Formula 1 may be used to form the HTL. The thickness of the HTL may be in the range of about 50 to 1000 Å, and preferably 100 to 600 Å. When the thickness of the HTL is less than 50 Å, a hole transporting ability of the HTL may be reduced. On the other hand, when the thickness of the HTL is greater than 1000 Å, the driving voltage of the device may be increased.

Then, an emitting layer (EML) can be formed on the HTL by vacuum deposition, spin coating, casting, LB, or the like. When the EML is formed by vacuum deposition or spin coating, the conditions for deposition and coating are similar to those for the formation of the HIL, although the conditions for deposition and coating may vary according to the material that is used to form the EML.

The thickness of the EML may be in the range of about 100 to 1000 Å, and preferably in the range of 200 to 600 Å. When the thickness of the EML is less than 100 Å, the emitting ability of the EML may be reduced. On the other hand, when the thickness of the EML is greater than 1000 Å, the driving voltage of the device may be increased.

A hole blocking layer (HBL) can be formed on the HTL by vacuum deposition, spin coating, casting, LB, or the like, to prevent diffusion of triplet excitons or holes into an electron transport layer when the phosphorescent dopant is used to form the EML. When the HBL is formed by vacuum deposition or spin coating, the conditions for deposition and coating are similar to those for the formation of the HIL, although the conditions for deposition and coating may vary according to the material that is used to form the HBL. The HBL may be formed of a known hole blocking material such as an oxadiazole derivative, a triazole derivative, a phenanthroline derivative, BCP or an aluminum complex.

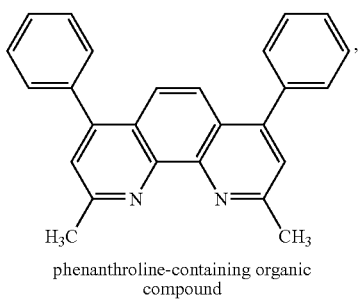

phenanthroline-containing organic compound

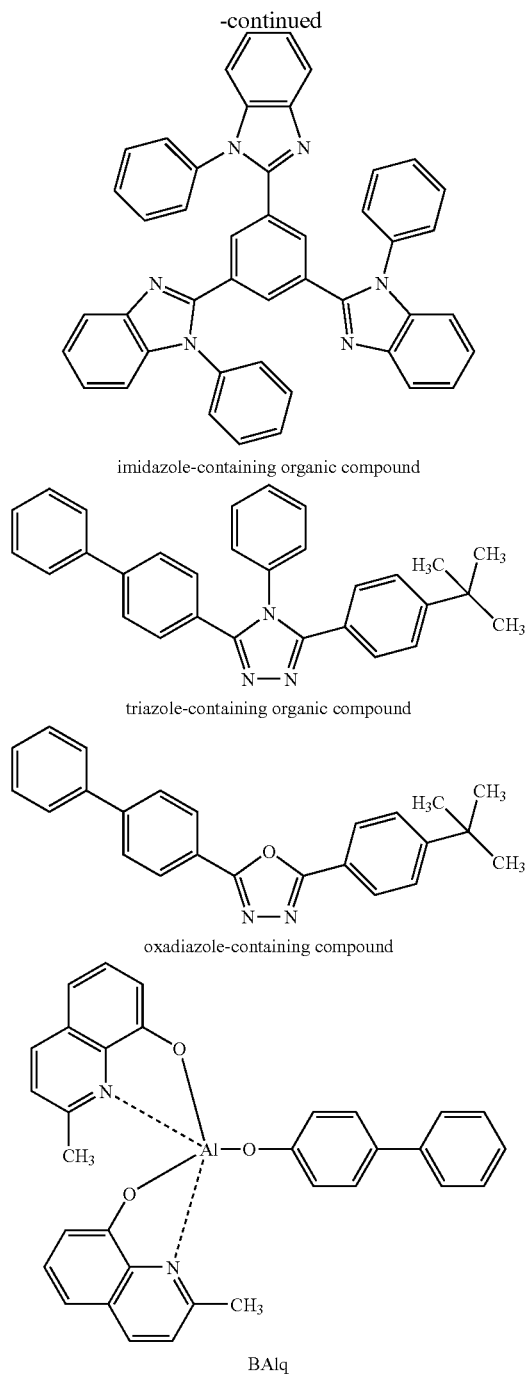

imidazole-containing organic compound triazole-containing organic compound oxadiazole-containing compound BAlq The thickness of the HBL may be in the range of about 50 to 1000 Å, and preferably in the range of 100 to 300 Å. When the thickness of the HBL is less than 50 Å, 11 the hole blocking ability of the HBL may be reduced. On the other hand, when the thickness of the HBL is greater than 1000 Å, the driving voltage of the device may be increased.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a known material in the art which stably transports injected electrons from a cathode, for example, an oxazole-based compound, an isooxazole-based compound, a triazole-based compound, an isothiazole-based compound, an oxadiazole-based compound, a thiadiazole-based compound, a perylene-based compound, an aluminum complex such as tris(8-quinolinolato)-aluminium (Alq3), BAlq, SAlq, Almq3, a gallium complex such as Gaq'2OPiv, Gaq'2OAc and 2(Gaq'2), or the like.

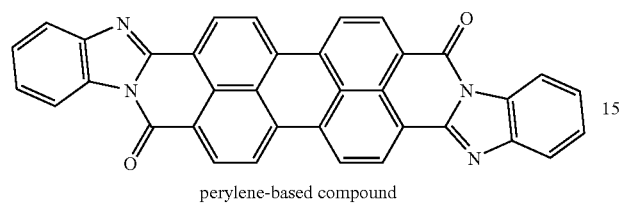

perylene-based compound

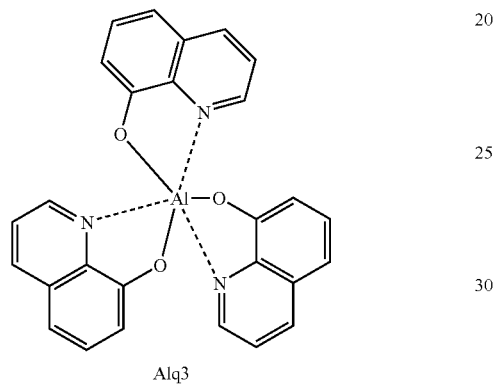

Alq3

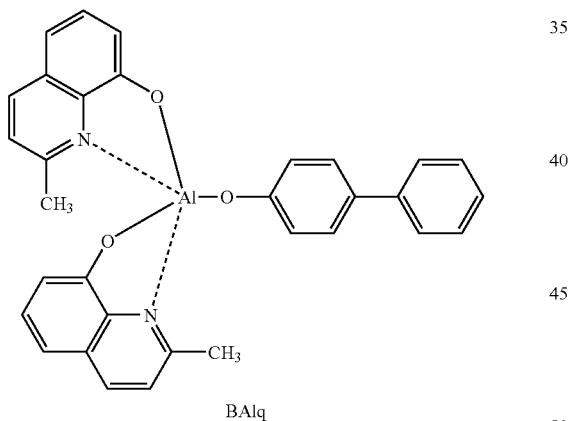

BAlq

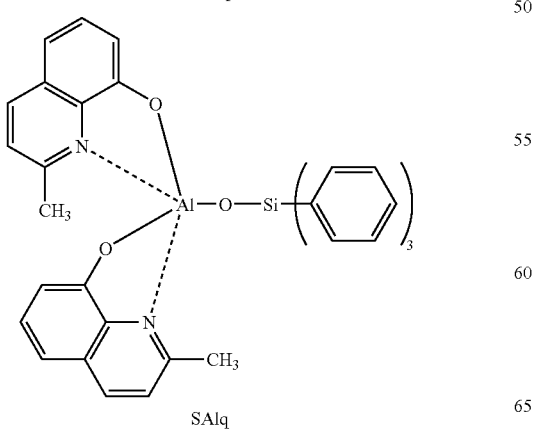

SAlq

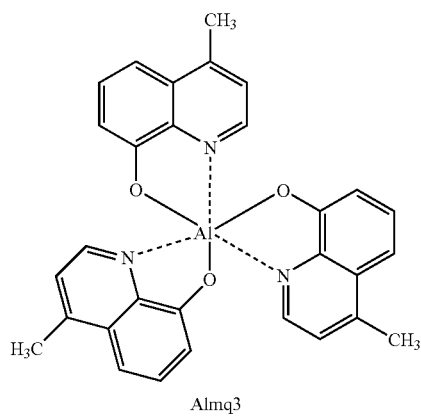

Almq3

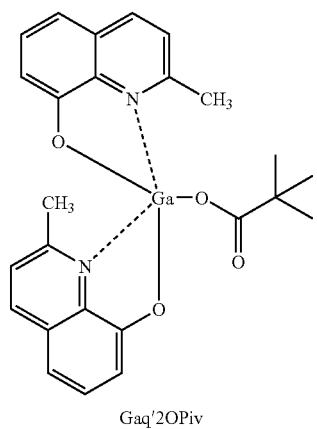

Gaq'2OPiv

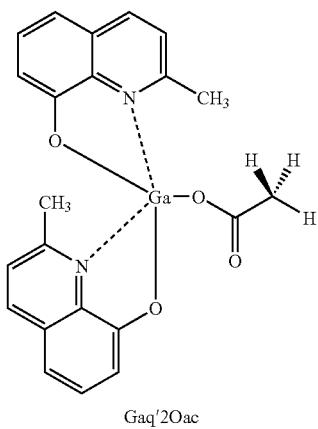

Gaq'2Oac

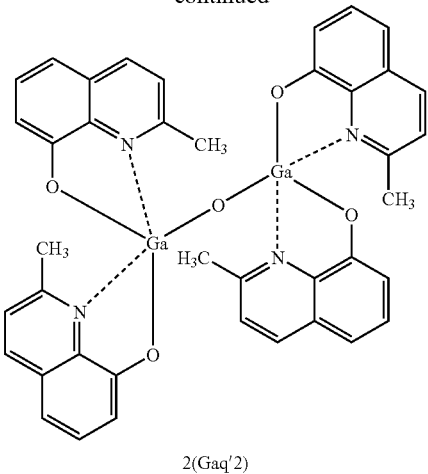

2(Gaq'2)

The thickness of the ETL may be in the range of about 100 to 1000 Å, and preferably 200 to 500 Å. When the thickness of the ETL is less than 100 Å, the electron transporting ability of the ETL may be reduced. On the other hand, when the thickness of the ETL is greater than 1000 Å, the driving voltage of the device may be increased.

Then, an electron injection layer (EIL), which is formed of a material allowing easy injection of electrons from a cathode, can be formed on the ETL. The material that is used to form the EIL is not limited.

The EIL may be formed of LiF, NaCl, CsF, $Li_2O$, BaO, or the like, which is known in the art. Conditions for the deposition of the EIL are, in general, similar to conditions for the formation of the HIL, although they may vary according to the material 11 that is used to form the EIL.

The thickness of the EIL may be in the range of about 1 to 100 Å, and preferably 5 to 50 Å. When the thickness of the EIL is less than 1 Å, the electron injecting ability of the EIL may be reduced. On the other hand, when the thickness of the EIL is greater than 100 Å, the driving voltage of the device may be increased.

Finally, a second electrode can be formed on the EIL by vacuum deposition, sputtering, or the like. The second electrode can be used as a cathode. The second electrode may be formed of a low work-function metal, an alloy, an electrically conductive compound, or a combination of these. In detail, the second electrode may be formed of Li, Mg, Al, Al—Li, Ca, Mg—In, Mg—Ag, or the like. Alternatively, a transparent cathode formed of ITO or IZO can be used to produce a top emission light emitting device.

Hereinafter, the present invention will be described in further detail with reference to the following examples. However, these synthesis examples and examples are given for the purpose of illustration and are not intended to limit the scope of the invention.

SYNTHESIS EXAMPLES

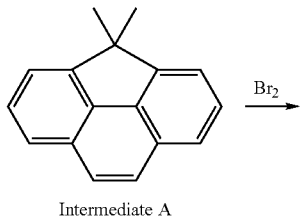

Intermediate A

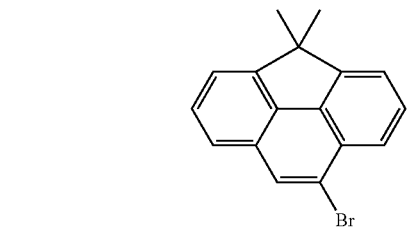

Compound 1

Synthesis Example 1

Synthesis of Compound 1

1) Synthesis of Intermediate A 5.6 g (29.7 mmol) of cyclopenta[def]phenanthrene was dissolved in 100 ml of DMSO in a 250 ml round-bottom flask, 0.5 g (0.1 eq, 2.97 mmol) of KI and 5.5 ml (3.0 eq, 89.2 mmol) of MeI were added thereto. The mixture was cooled to about 10° C. and 9.7 g (5.0 eq, 148 mmol) of powdered KOH (85%) was gradually added to the mixture. After 1 hour, the mixture was heated to room temperature and stirred for 10 hours. The reaction solution was subject to extraction using an EtOAc-Hex (1:1) solution, dried using anhydrous sodium sulfate, filtered and concentrated. The resultant was purified 2 to 3 times with a silica gel column chromatography (n-Hex) to separate a compound obtained. A solid obtained therefrom was recrystallized using MeOH to obtain 6.6 g of white solid (Yield: 75%)

3) Synthesis of Compound 1

5.0 g (22.9 mmol) of Intermediate A was dissolved in 100 ml of $CCl_4$ in a 250 ml round-bottom flask. The mixture was cooled to 0° C. and 3.3 g (20.8 mmol) of $Br_2$ was added thereto. After 4 hours of reaction, 10% $NaSO_3$ solution was added to the mixture to separate an organic layer. The separated organic layer was concentrated in a reduced pressure and recrystallized using n-hexane to obtain 4.9 g of Compound 1.

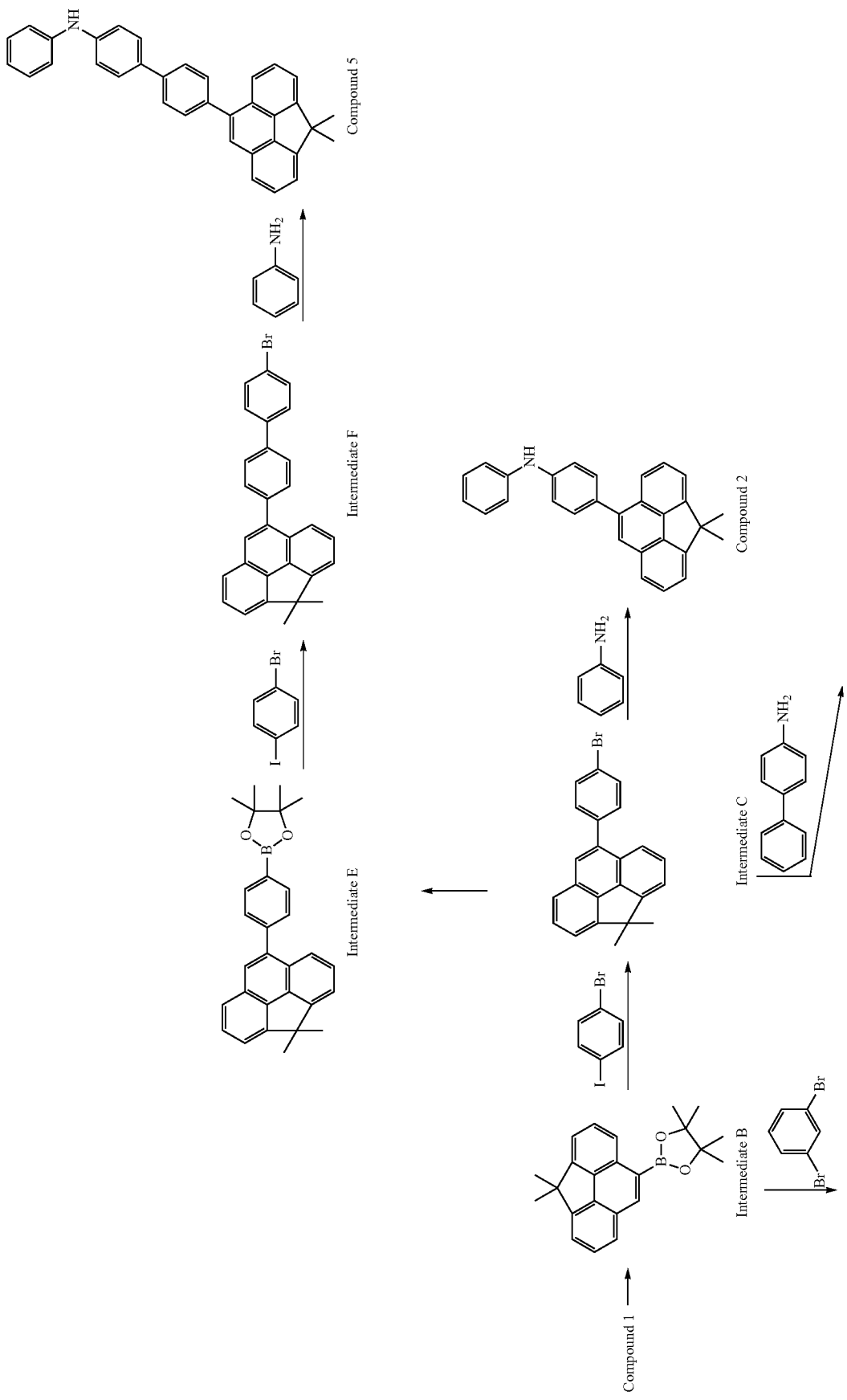

-continued
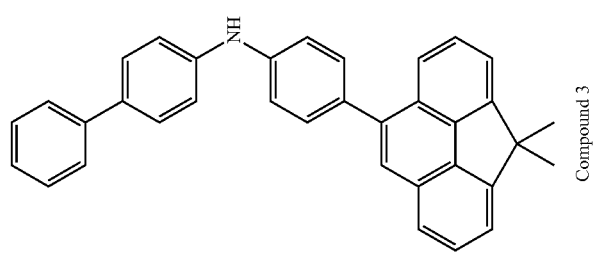
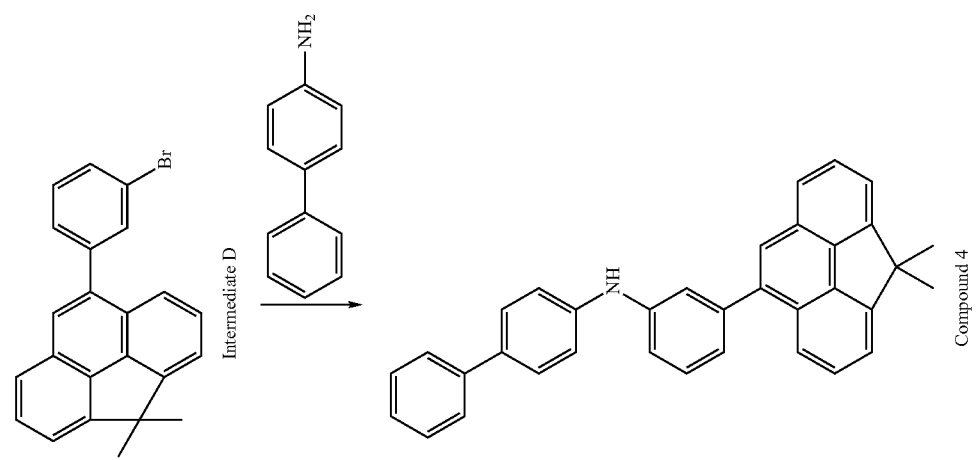

Synthesis Example 2

Synthesis of Compound 2

1) Synthesis of Intermediate B 2.0 g (6.72 mmol) of Compound 1 was dissolved in 20 ml of anhydrous THF in a 50 ml round-bottom flask and the flask was cooled to −78° C. 4.0 ml of 2.5 M nBuLi was gradually added to the mixture and the mixture was stirred for 1 hour. Then, 2.75 ml (13.3 mmol) of 2-isopropoxy-4,4,5,5-tetramethyl-1,3,2-dioxaborolane dissolved in 10 ml of anhydrous THF was added thereto for 30 minutes. When the reaction is completed, the reaction solution was concentrated in a reduced pressure and ethyl acetate and a NaCl solution were added thereto to separate an organic layer. The concentrated resultant was separated using a silica gel chromatography to obtain 1.27 g of Intermediate B.

2) Synthesis of Intermediate C 1.0 g (2.9 mmol) of Intermediate B, 1.6 g (5.8 mmol) of 4-iodobromobenzene, 0.1 g of tetrakis(triphenylphosphine) palladium(0), 2.85 ml of 2 M $K_2CO_3$, and 0.65 g tetrabutylammoniumbromide were added to a 100 ml of round-bottom flask in an argon atmosphere, and 50 ml of THF and 20 ml of toluene were added thereto. The mixture was refluxed at 100° C. for 16 hours. When the mixture solution turned dark brown, water was added thereto and the mixture was subject to extraction using ethyl acetate. Then, an organic layer extracted therefrom was dried using anhydrous magnesium sulfate and filtered to remove a solvent. The resultant was dissolved in a small amount of toluene and separated using a silica gel column chromatography to obtain 0.72 g of Intermediate C (Yield: 74%) which was identified by atmospheric pressure chemical ionization (APCI) using LCMS (SHIMADZU, LCMS-IT-TOF). As a result, a main peak was observed at [M+H]+=374.

3) Synthesis of Compound 2

1.0 g (2.67 mmol) of Intermediate D, 0.25 g (2.67 mmol) of aniline, 0.28 g sodium tert-butoxide, 0.05 g of tris(dibenzylidine acetone) dipalladium(0) (Pd(dba)$_2$) and 0.05 g of tri(tert-butyl)phosphine were dissolved in 30 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 0.92 g of Compound 2 which was identified by APCI using LCMS. As a result, a main peak was observed at [M+H]+=386.

Synthesis Example 3

Synthesis of Compound 3

1.0 g (2.67 mmol) of Intermediate C, 1.8 g (10.68 mmol) of 4-biphenylamine, 0.28 g sodium tert-butoxide, 0.05 g of tris(dibenzylidine acetone) dipalladium(0) (Pd(dba)$_2$) and 0.05 g of tri(tert-butyl)phosphine were dissolved in 30 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 1.14 g of solid Compound 3 which was identified by APCI using LCMS. As a result, a main peak was observed at [M+H]+=462.

Synthesis Example 4

Synthesis of Compound 4

1) Synthesis of Intermediate D 1.0 g (2.9 mmol) of Intermediate B, 2.7 g (11.6 mmol) of 1,3-dibromobezene, 0.1 g of tetrakis(triphenylphosphine) palladium(0), 2.85 ml of 2 M $K_2CO_3$, and 0.65 g tetrabutylammoniumbromide were added to a 100 ml of round-bottom flask in an argon atmosphere, and 50 ml of THF and 20 ml of toluene were added thereto. The mixture was refluxed at 100° C. for 16 hours. When the mixture solution turned dark brown, water was added thereto and the mixture was subject to extraction using ethyl acetate. Then, an organic layer extracted therefrom was dried using anhydrous magnesium sulfate and filtered to remove a solvent. The resultant was dissolved in a small amount of toluene and separated using a silica gel column chromatography to obtain 0.73 g of Intermediate D which was identified by atmospheric pressure chemical ionization (APCI) using LCMS (SHIMADZU, LCMS-IT-TOF). As a result, a main peak was observed at [M+H]+=374.

3) Synthesis of Compound 4

Compound 4 was synthesized in the same manner as in Synthesis Example 3, except that Intermediate D was used instead of Intermediate C. Compound 4 was identified by atmospheric pressure chemical ionization (APCI) using LCMS (SHIMADZU, LCMS-IT-TOF). As a result, a main peak was observed at [M+H]+=462.

Synthesis Example 5

Synthesis of Compound 5

1) Synthesis of Intermediate E

Intermediate E was synthesized in the same manner as in Synthesis Example 2-1), except that Intermediate C was used instead of Compound 1.

2) Synthesis of Intermediate F

Intermediate F was synthesized in the same manner as in Synthesis Example 2-2), except that Intermediate E was used instead of Intermediate B.

3) Synthesis of Compound 5

Compound 5 was synthesized in the same manner as in Synthesis Example 2-3), except that Intermediate F was used instead of Intermediate D.

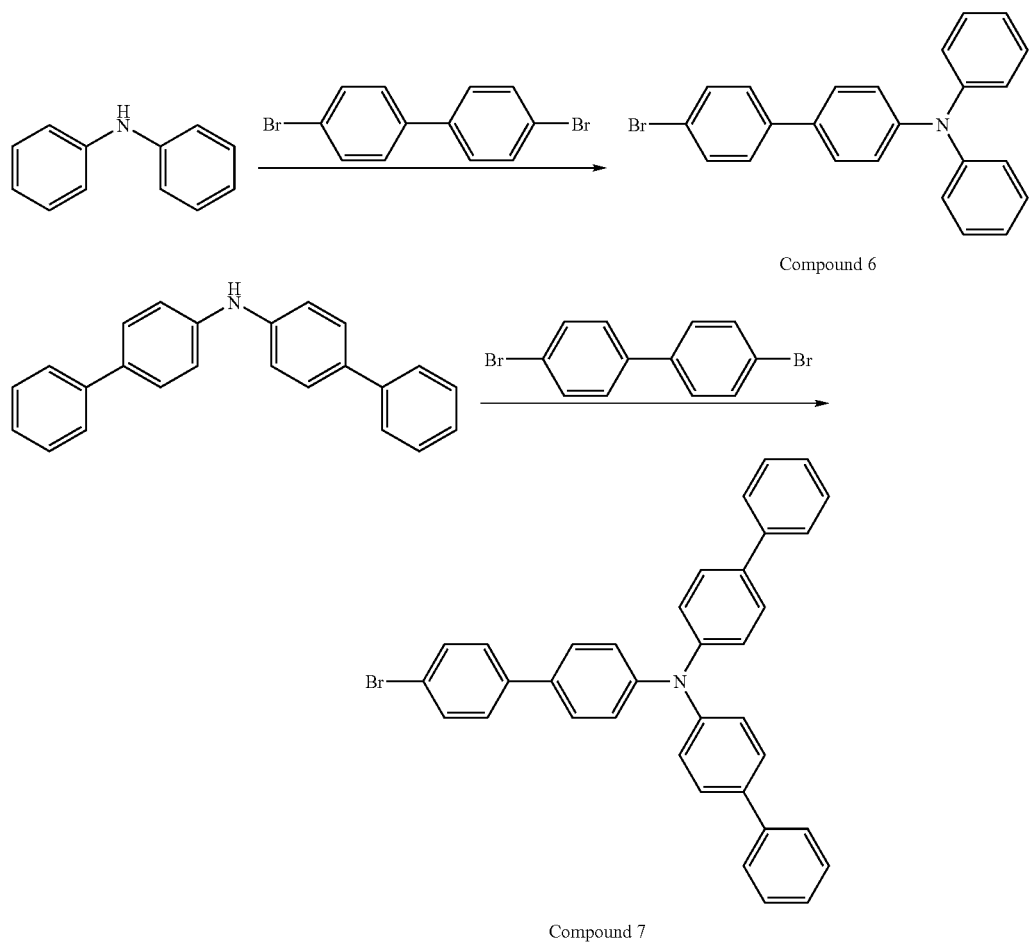

Compound 6

Compound 7

Synthesis Example 6

Synthesis of Compound 6

1.94 g (6.22 mmol) of 4,4-dibromobiphenyl, 0.53 g (3.11 mmol) of biphenyl amine, 0.45 g sodium tert-butoxide, 0.03 g of tris(dibenzylidine acetone)dipalladium(0) (Pd(dba)$_2$) and 0.01 g of tri(tert-butyl)phosphine were dissolved in 30 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 0.6 g of solid Compound 6 (Yield: 48%) which was identified by APCI using LCMS. As a result, a main peak was observed at [M+H]+=400.

Synthesis Example 7

Synthesis of Compound 7

1.46 g (4.67 mmol) of 4,4-dibromobiphenyl, 1.0 g (3.11 mmol) of bisbiphenyl amine, 0.3 g sodium tert-butoxide, 0.05 g of tris(dibenzylidine acetone)dipalladium(0) (Pd(dba)$_2$) and 0.05 g of tri(tert-butyl)phosphine were dissolved in 30 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 0.42 g of solid Compound 7 which was identified by APCI using LCMS. As a result, a main peak was observed at [M+H]+=552.

EXAMPLES

Hereinafter, a method of preparing a cyclopentaphenanthrene-based compound according to an embodiment of the present invention will be described.

Example 1

Synthesis of a Compound Represented by Formula 11

1.0 g (2.97 mmol) of N,N-diphenylbenzidine, 2.8 g (7.43 mmol) of Intermediate C, 0.8 g sodium tert-butoxide, 0. 3 g of tris(dibenzylidine acetone)dipalladium(0) (Pd(dba)$_2$) and 0.07 g of tri(tert-butyl)phosphine were dissolved in 50 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 0.91 g of a solid compound represented by Formula 11 which was identified by APCI using LCMS. As a result, a main peak was observed at [M+H]+=921.

Example 2

Synthesis of a Compound Represented by Formula 12

1.0 g (2.5 mmol) of Compound 6, 1.2 g (2.6 mmol) of Compound 5, 0.41 g sodium tert-butoxide, 0.09 g of tris(dibenzylidine acetone) dipalladium(0) (Pd(dba)$_2$) and 0.03 g of tri(tert-butyl)phosphine were dissolved in 50 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 1.7 g of a solid compound represented by Formula 12 which was identified by APCI using LCMS. As a result, a main peak was observed at [M+H]+=781.

Example 3

Synthesis of a Compound Represented by Formula 14

Figure 2:
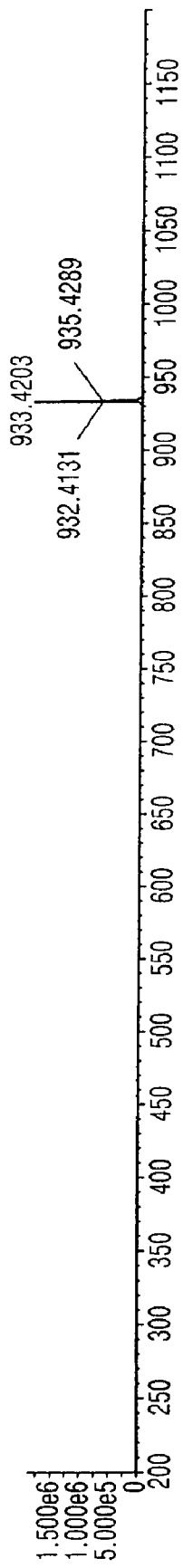
FIG. 2 is a graph illustrating LCMS results of a compound prepared according to Example 3.

1.0 g (2.16 mmol) of Compound 7, 1.43 g (2.6 mmol) of Compound 3, 0.41 g sodium tert-butoxide, 0.09 g of tris(dibenzylidine acetone) dipalladium(0) (Pd(dba)$_2$) and 0.03 g of tri(tert-butyl)phosphine were dissolved in 50 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 1.8 g of a solid compound represented by Formula 14 which was identified by APCI using LCMS. As a result, a main peak was observed at [M$_+$H]+=933. FIG. 2 is a graph illustrating LCMS results of the compound prepared according to Example 3.

Example 4

Synthesis of a Compound Represented by Formula 15

1.0 g (2.59 mmol) of Compound 2, 1.43 g (2.6 mmol) of Compound 3, 0.7 g sodium tert-butoxide, 0.1 g of tris(dibenzylidine acetone) dipalladium(0) (Pd(dba)$_2$) and 0.03 g of tri(tert-butyl)phosphine were dissolved in 50 ml of toluene in a 50 ml of round-bottom flask, and the mixture was refluxed for 12 hours. When the reaction is completed, the mixture was cooled to room temperature and 100 ml of distilled water was added thereto to extract an organic layer. The collected organic layer was dried using MgSO$_4$, concentrated and separated using a silica gel chromatography. An elute solution obtained therefrom was concentrated and dried to obtain 1.3 g of a solid compound represented by Formula 15 (Yield: 71%) which was identified by APCI using LCMS. As a result, a main peak was observed at [M+H]+=857.

Example 5

Synthesis of a Compound Represented by Formula 21

A compound represented by Formula 21 was synthesized in the same manner as in Example 3, except that Compound 4 was used instead of Compound 3 which was identified by APCI using LCMS. As a result, a main peak was observed at [M+H]+=933.

Hereinafter, manufacturing and evaluating organic light emitting devices according to an embodiment of the present invention will be described.

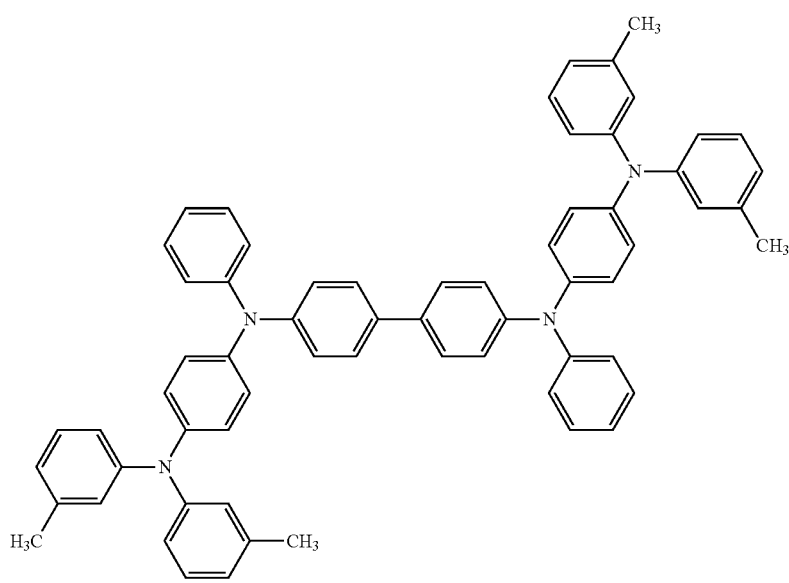

Formula 41

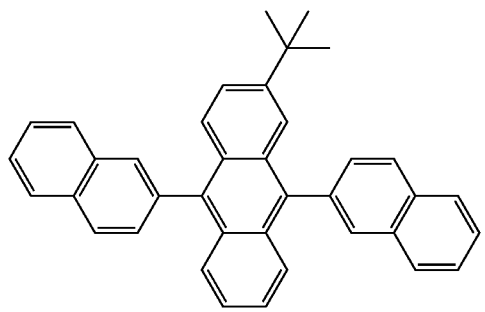

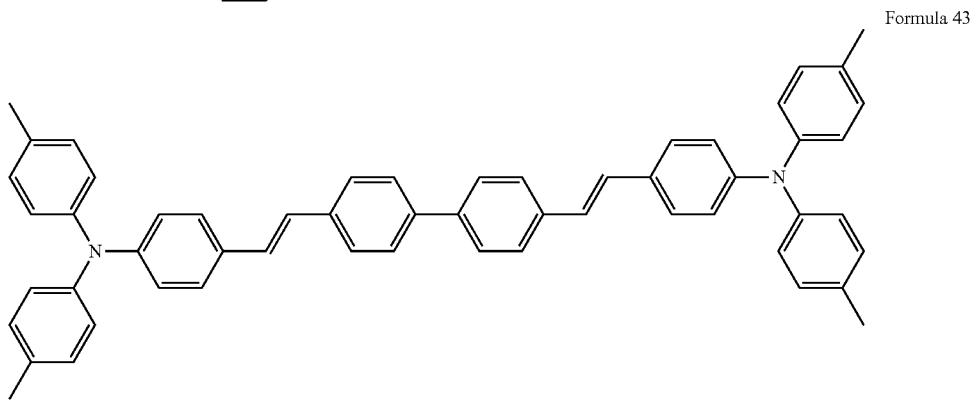

Formula 42

Formula 43

Example 6

Manufacturing and Evaluating Organic Light Emitting Devices

An organic light emitting device having the following structure was manufactured using a compound represented by Formula 41 as a hole injection layer, a compound represented by Formula 11 of Example 1 as a hole transport layer, a compound represented by Formula 42 as a host of an emitting layer and a compound represented by Formula 43 as a dopant of the emitting layer: ITO/compound of Formula 41 (600 Å)/compound of Formula 11 (300 Å)/compound of Formula 42: compound of Formula 43 (300 Å)/Alq3(25 Å)/LiF(6 Å)/Al(2000 Å).

A 15 Ω/cm² (1000 Å) ITO glass substrate was cut to a size of 50 mm×50 mm×0.7 mm, microwave washed with acetone isopropyl alcohol for 15 minutes, microwave washed with pure water for 15 minutes, and washed with UV ozone for 30 minutes to prepare an anode. The compound of Formula 41 was vacuum deposited on the substrate to form a hole injection layer and the compound of Formula 11 was vacuum deposited thereon to form a hole transport layer. Then, the compounds of Formulae 42 and 43 were vacuum deposited in a weight ratio of 100:5 to form an emitting layer. Then, Alq3 was vacuum deposited on the emitting layer to form an electron transport layer with a thickness of 25 Å. LiF was vacuum deposited on the electron transport layer to form an electron injection layer with a thickness of 6 Å and Al was vacuum deposited on the electron injection layer to form a cathode with a thickness of 2000 Å. As a result, an organic light emitting device illustrated in FIG. 1A was manufactured.

The obtained organic light emitting device had 13,000 cd/m² of blue light emitting at 6.0 V and emitting efficiency was 6.91 cd/A. The results are shown in Table 1.

Examples 7 to 10

Manufacturing and Evaluating Organic Light Emitting Devices

Organic light emitting devices were prepared in the same manner as in Example 6, except that compounds synthesized according to Examples 2 to 5 were respectively used instead of the compound of Formula 11 synthesized according to Example 1 as a hole transport layer. Brightness and emitting efficiency of the organic light emitting devices were measured when the organic light emitting devices were driven at 6 V and the results are shown in Table 1.

Comparative Example 1

Manufacturing and Evaluating Organic Light Emitting Devices

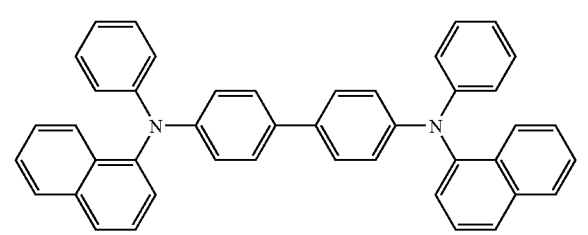

Formula 44

An organic light emitting device was prepared in the same manner as in Example 6, except that a compound represented by Formula 44 was used instead of the compound of Formula 11 synthesized according to Example 1 as a hole transport layer. Driving voltage, emitting efficiency and brightness-half life of the organic light emitting device were measured when the organic light emitting devices were driven at a constant current of 30 mA/cm² and the results are shown in Table 1.

TABLE 1

| Compound | | Driving voltage (V) | Emitting efficiency (cd/A) | Brightness half-life (hr) |
|---|---|---|---|---|
| Example 6 | Example 1 (Formula 11) | 7.2 | 6.6 | 1100 |
| Example 7 | Example 2 (Formula 12) | 6.8 | 6.7 | 1090 |
| Example 8 | Example 3 (Formula 14) | 7.1 | 6.8 | 1340 |
| Example 9 | Example 4 (Formula 15) | 7.2 | 6.8 | 1300 |
| Example 10 | Example 5 (Formula 21) | 7.0 | 6.9 | 1330 |
| Comparative Example 1 | Formula 44 | 7.3 | 6.2 | 920 |

Referring to Table 1, it can be seen that the organic light emitting devices prepared according to Examples 6 to 10 have improved brightness and emitting efficiency compared to the organic light emitting device of Comparative Example 1. Thus, the cyclopentaphenanthrene-based compound according to the present invention has excellent hole transporting capability and high thermal stability.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cyclopentaphenanthrene-based compound represented by Formula 1 below:

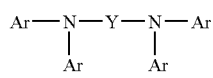

Formula 1 wherein Y is a bivalent linking group and selected from the group consisting of a substituted or unsubstituted C6-C30 arylene group and a substituted or unsubstituted C2-C30 heteroarylene group;

at least one of the Ar groups is a substituent represented by Formula 7 or 8 below, and the others, which are identical to or different from each other, are a substituted or unsubstituted C6-C30 aryl group:

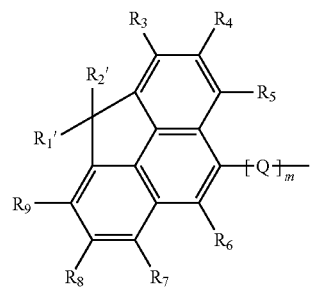

Formula 7

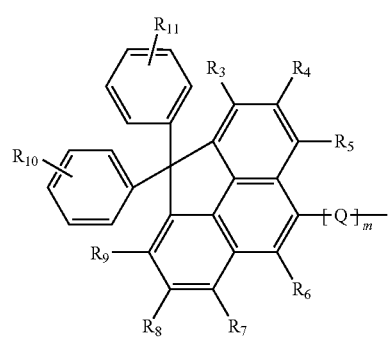

Formula 8 wherein $R_1'$, $R_2'$, $R_{10}$ and $R_{11}$ are each independently selected from the group consisting of a hydrogen atom a halogen atom a cyano group, a hydroxyl group a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group a substituted or unsubstituted C6-C30 aralkyl group and a substituted or unsubstituted C2-C30 heteroaryl group; and $R_3$ to $R_9$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

m is 1, 2 or 3; and

Q is a bivalent group represented by one of the formulae below:

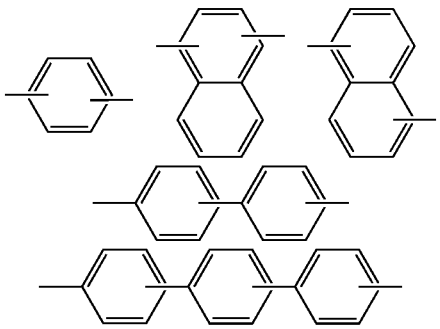

-continued

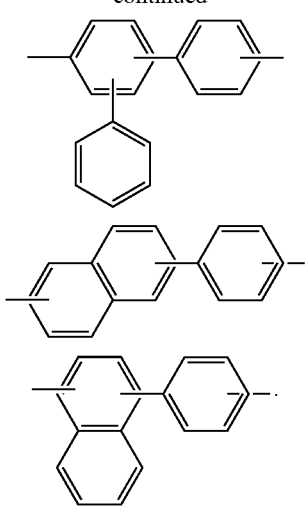

2. The cyclopentaphenanthrene-based compound of claim 1, wherein at least one of Ar groups is a substituent represented by Formula 7, which is represented by any one of Formulae 3 to 6 below:

Formula 3

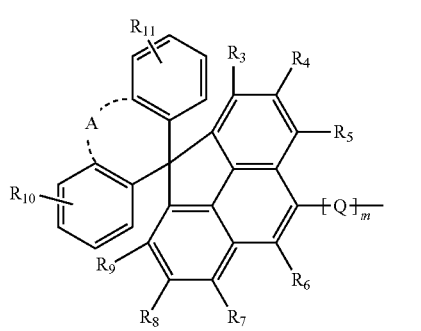

Formula 4

Formula 5

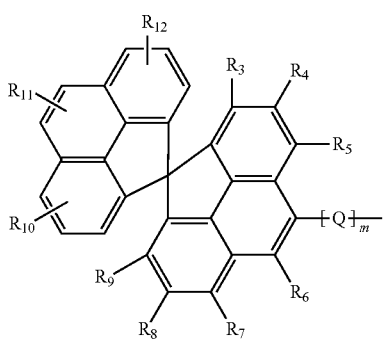

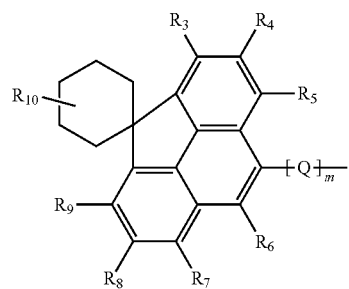

-continued

Formula 6

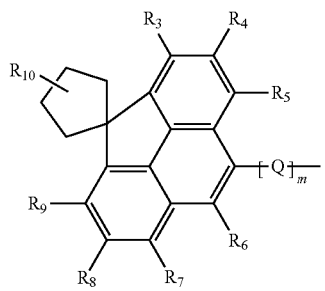

wherein $R_{10}$ to $R_{12}$ is selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

A is an oxygen atom, a sulfur atom or —$(CH_2)_p$—, wherein p is an integer of 1 to 5; and $R_3$ to $R_9$ are each independently selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group and a substituted or unsubstituted C2-C30 heteroaryl group;

m is 1, 2 or 3; and

Q is a bivalent group represented by one of the formulae below:

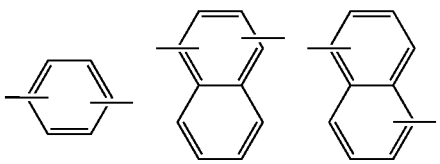

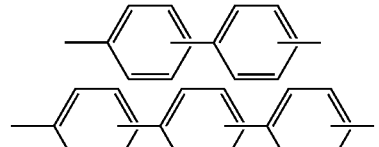

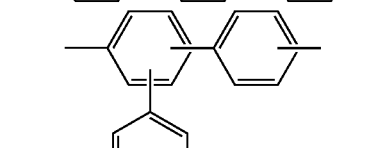

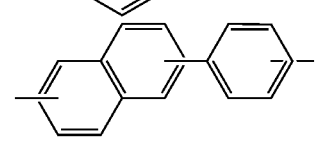

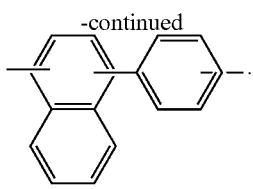

3. The cyclopentaphenanthrene-based compound of claim 1, wherein Y is a bivalent linking group represented by any one of the compounds represented by formulae below:

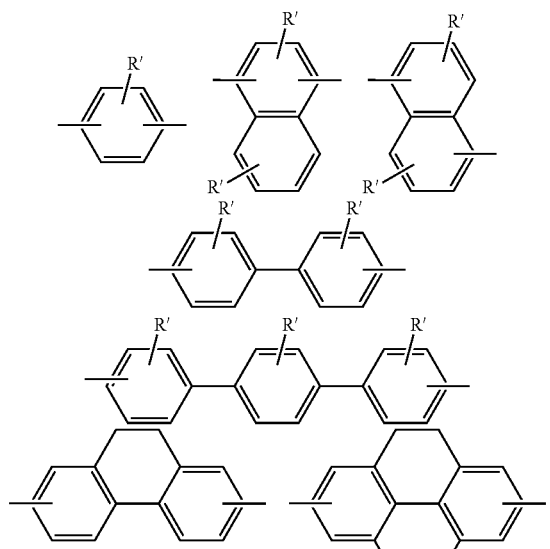

wherein R' is selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group and a substituted or unsubstituted C1-C20 alkoxy group.

4. The cyclopentaphenanthrene-based compound of claim 1, wherein at least one of the Ar groups is a substituent represented by Formula 7 or 8, and the others, which are identical to or different from each other, are selected from the group consisting of the formulae below:

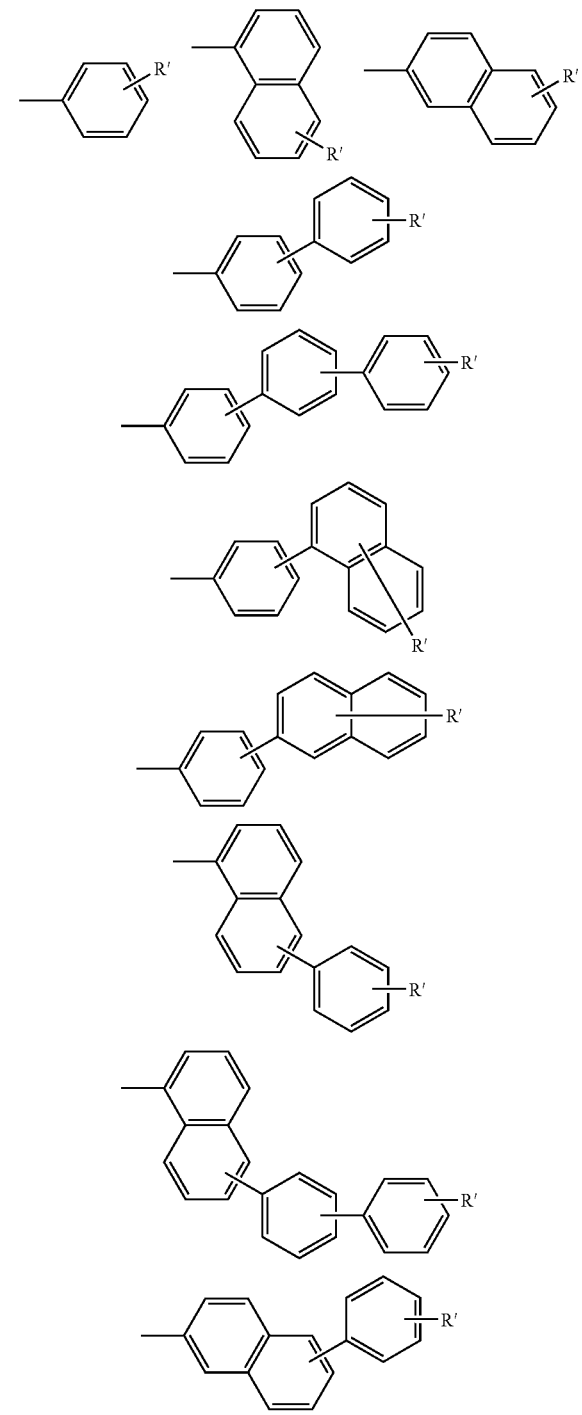

51
-continued

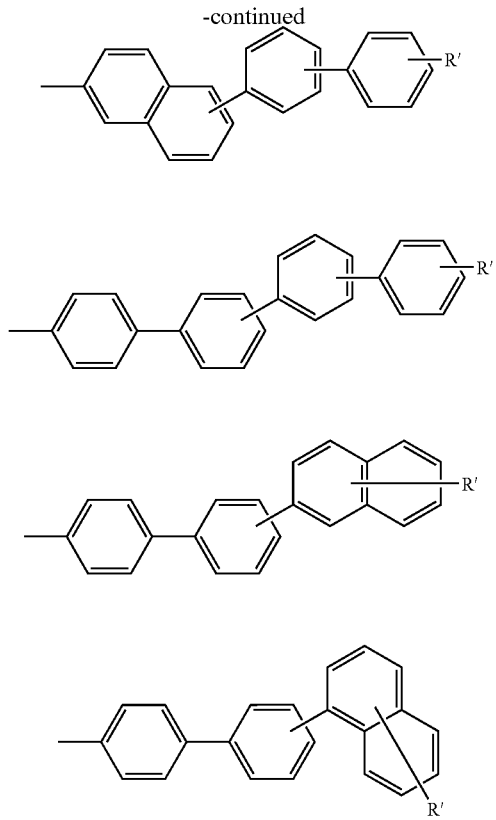

52
-continued

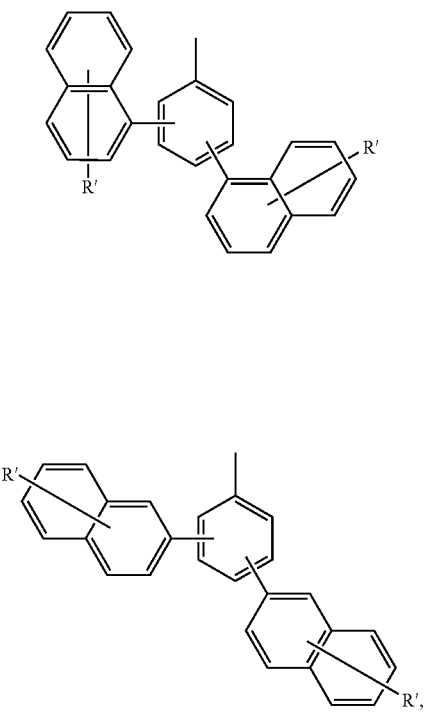

wherein R' is selected from the group consisting of a hydrogen atom, a halogen atom, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group and a substituted or unsubstituted C1-C20 alkoxy group.

5. The cyclopentaphenanthrene-based compound of claim 1, being one of the compounds represented by Formulae 10 to 32, and 35 to 40 below:

Formula 10

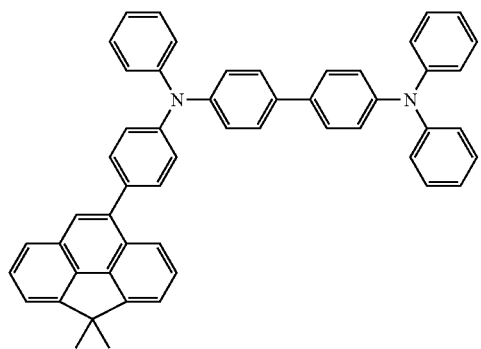

Formula 11

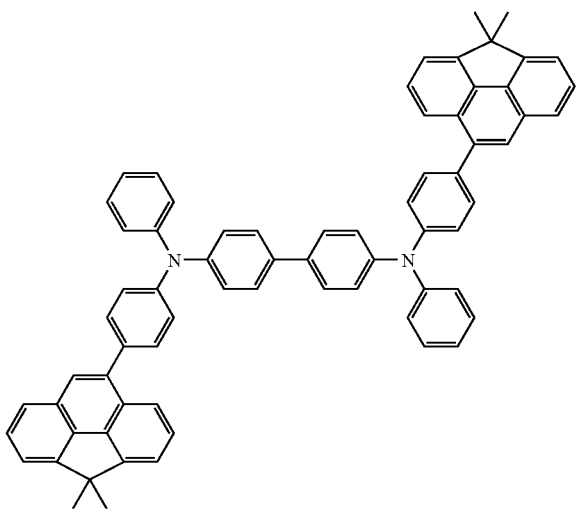

-continued
Formula 12
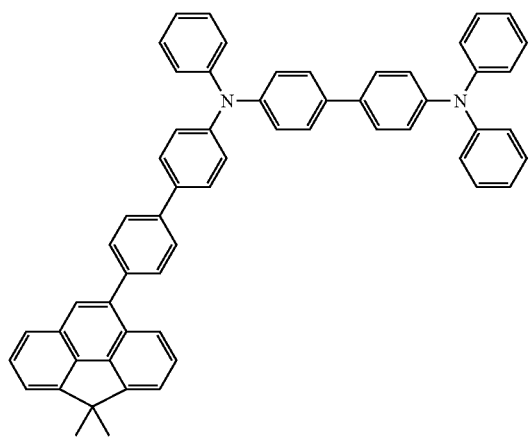
Formula 13
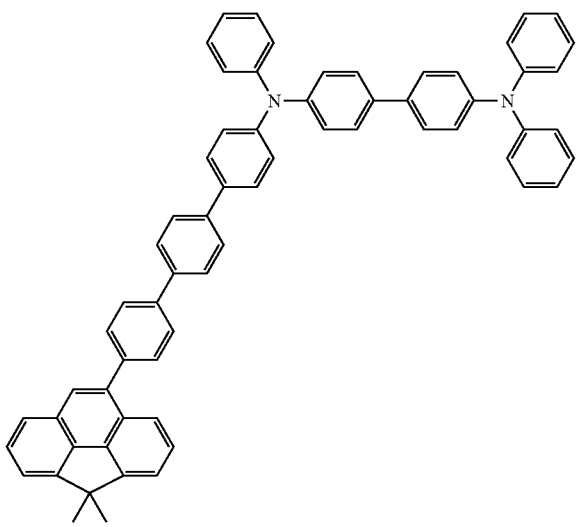
Formula 14
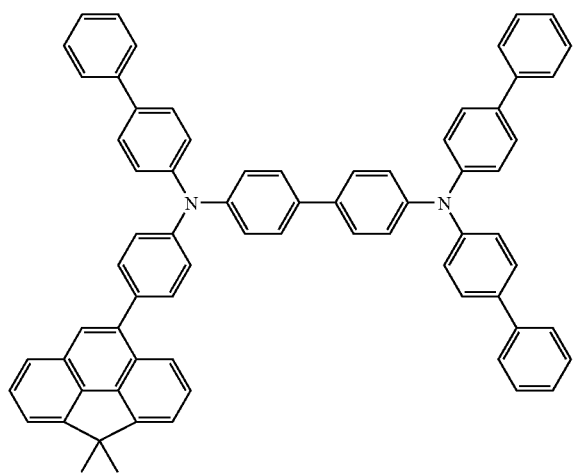
Formula 15
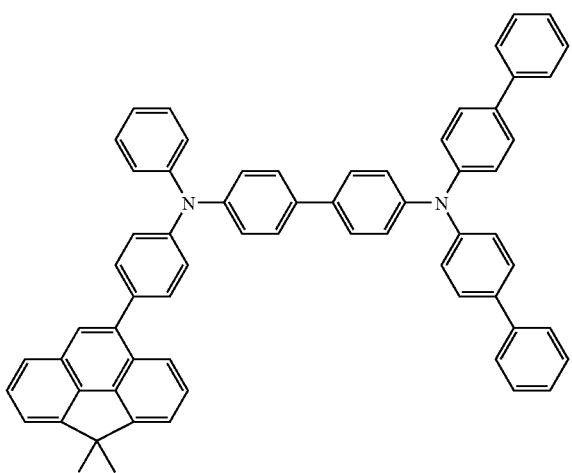
Formula 16
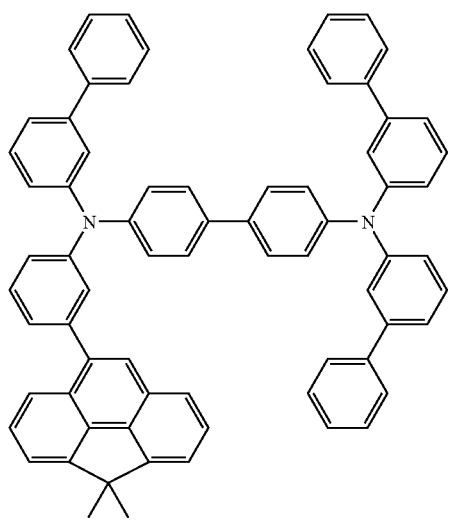
Formula 17
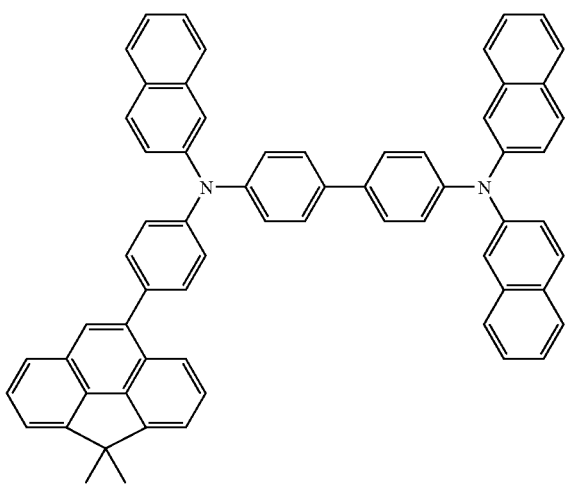

Formula 18
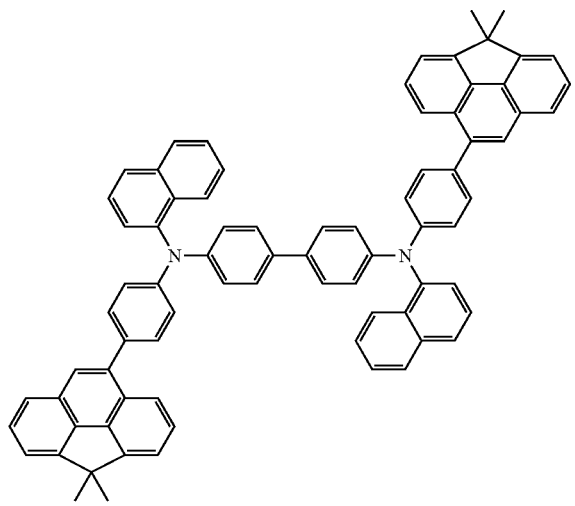
Formula 19
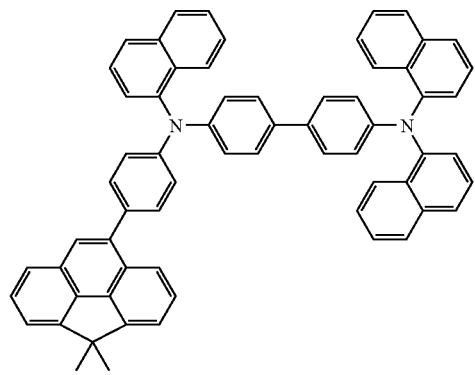
Formula 20
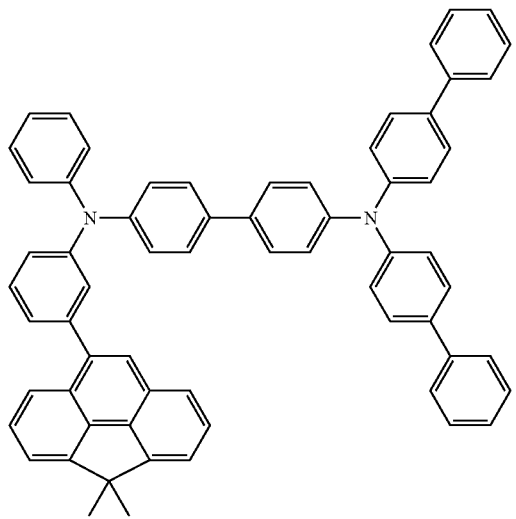
Formula 21
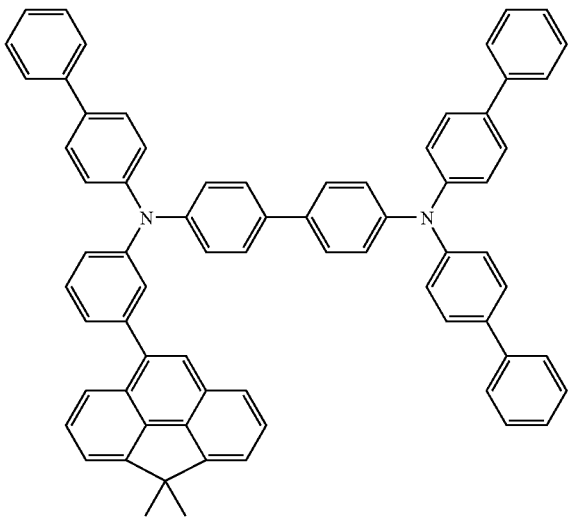
Formula 22
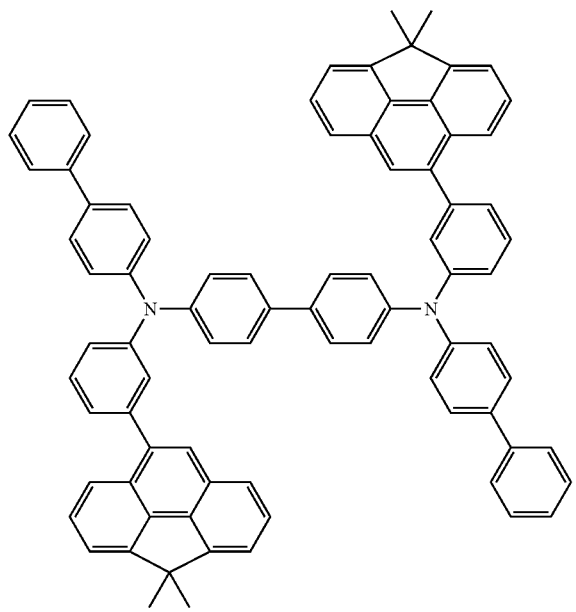
Formula 23
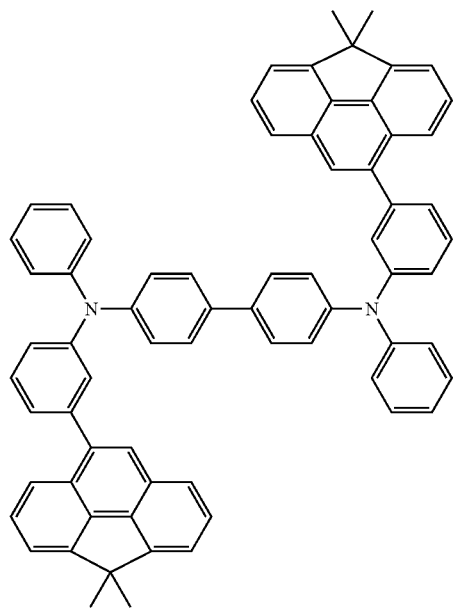

-continued
Formula 24
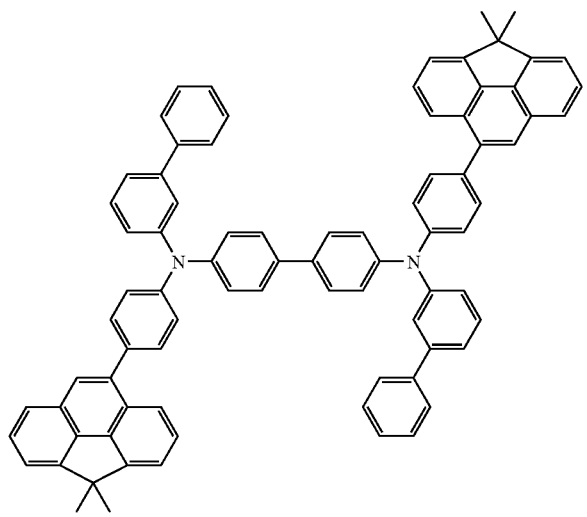
Formula 25
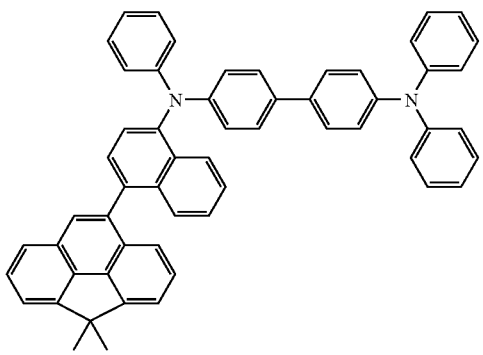
Formula 26
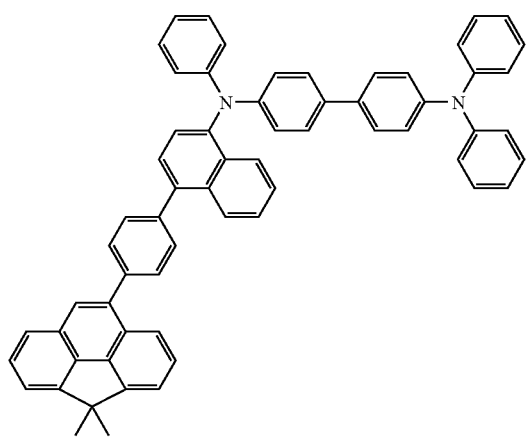
Formula 27
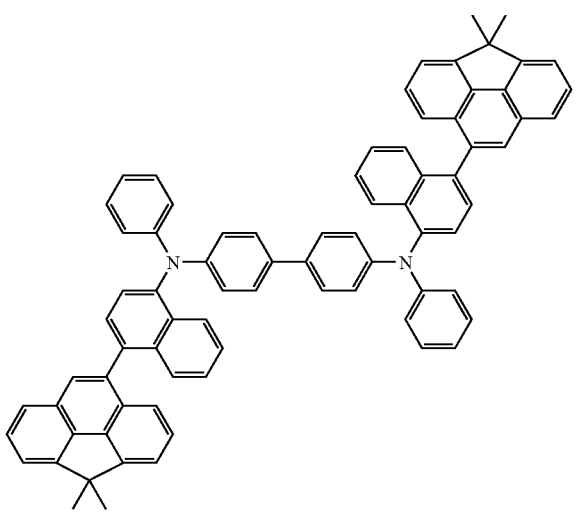
Formula 28
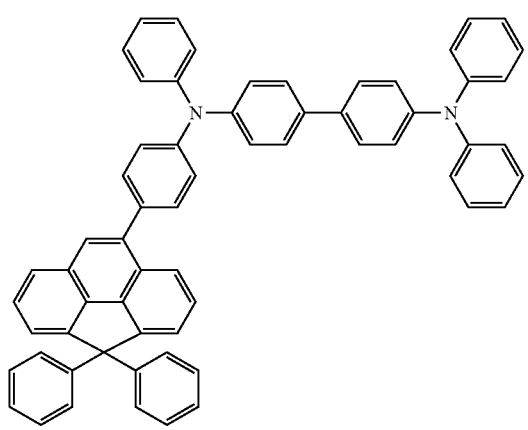
Formula 29
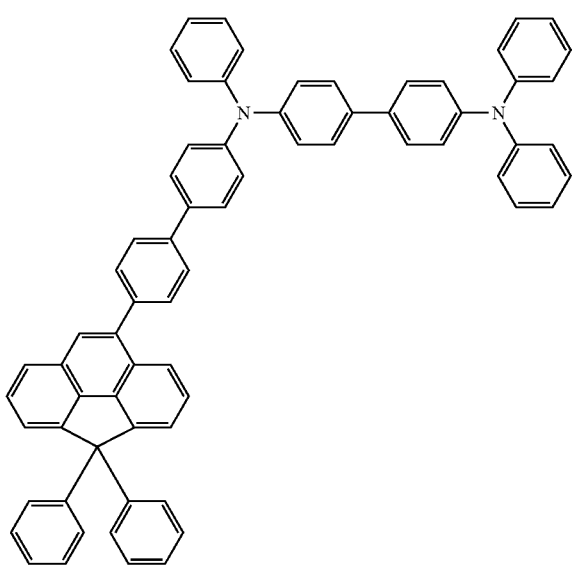

Formula 30
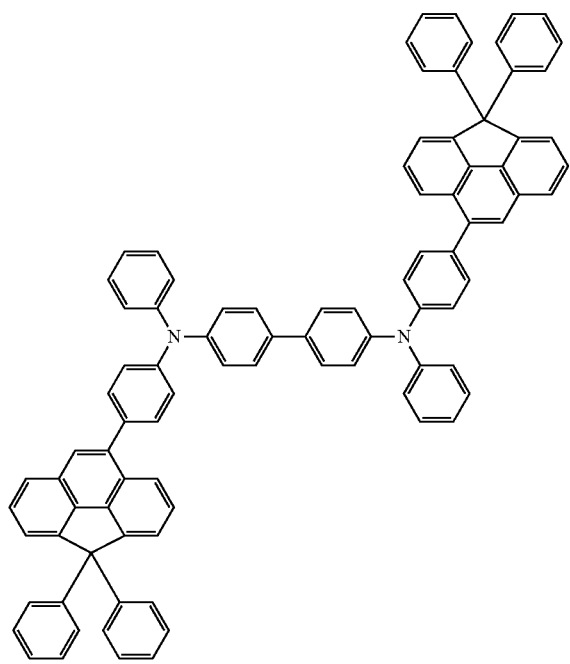
Formula 31
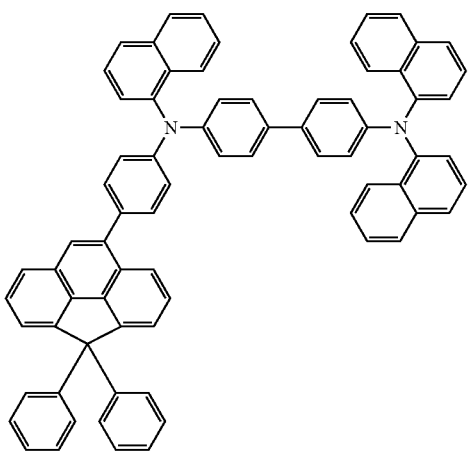
Formula 32
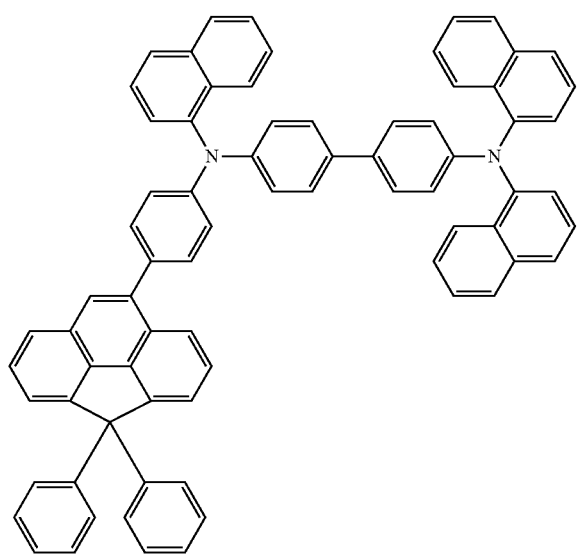

Formula 35
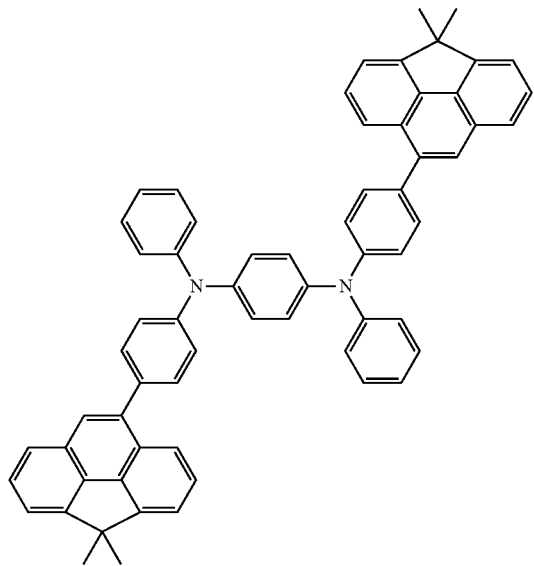
Formula 36
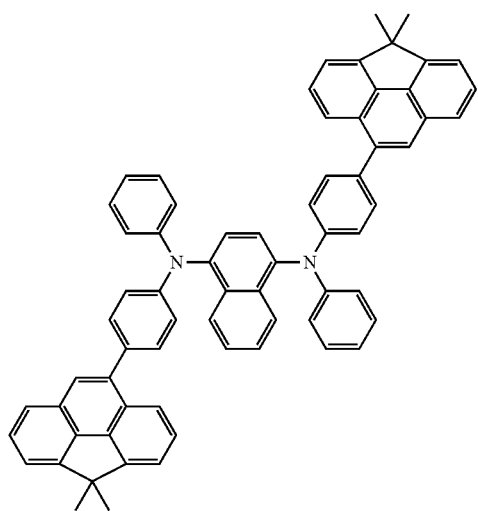
Formula 37
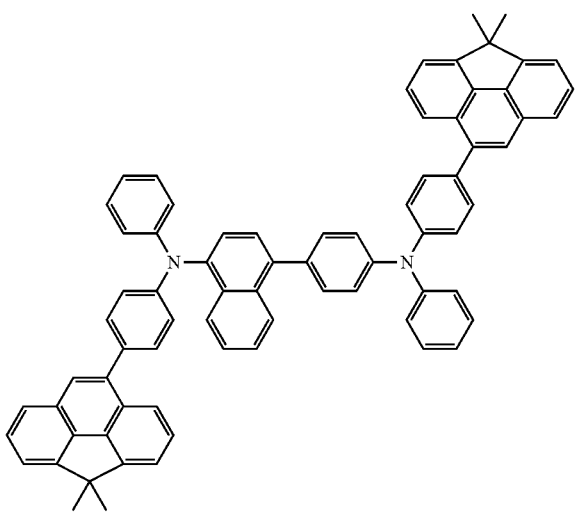

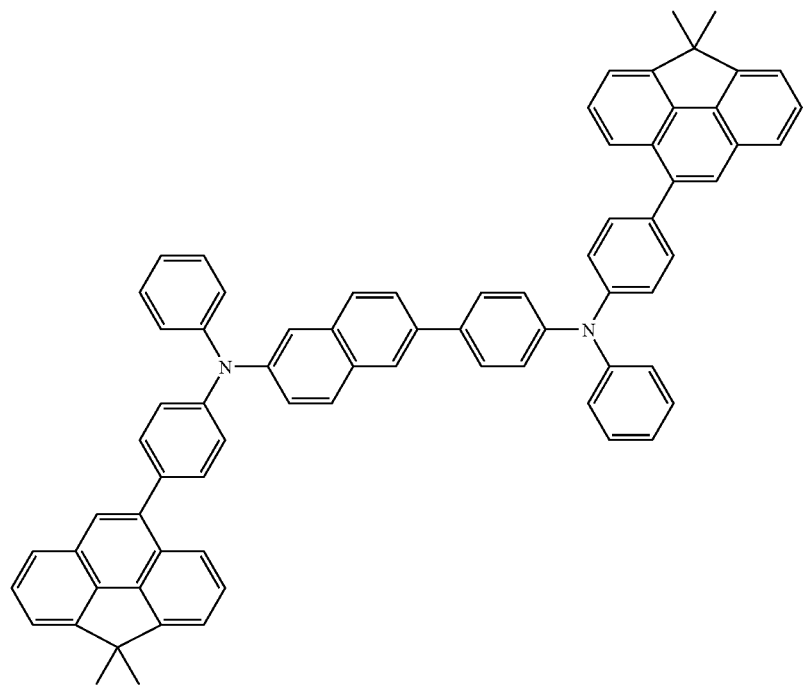
Formula 38
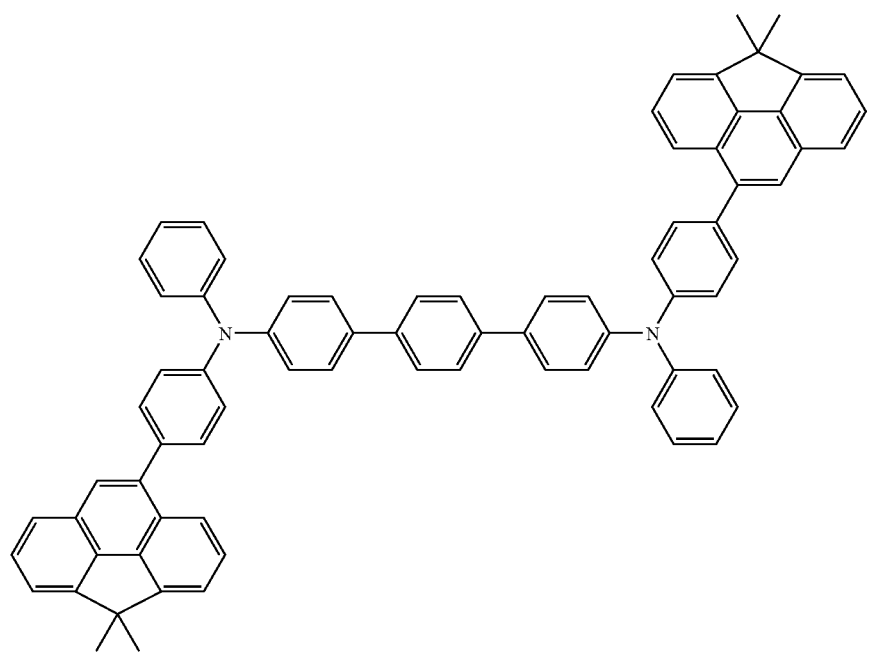
Formula 39

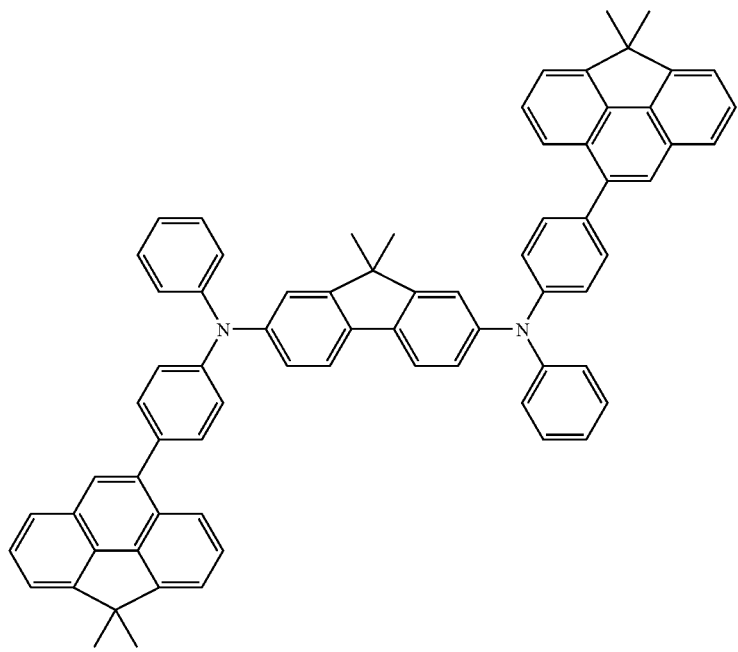

Formula 40

6. An organic light emitting device comprising:
a first electrode;
a second electrode; and
at least one organic layer between the first electrode and the second electrode,
wherein the organic layer comprises a compound according to any one of the claims 1, 2, 3, 4, or 5.

7. The organic light emitting device of claim 6, wherein the organic layer is selected from the group consisting of an emitting layer, a hole injection layer and a hole transport layer.

8. The organic light emitting device of claim 6, wherein the organic layer is a hole transport layer.

9. The organic light emitting device of claim 6, further comprising at least one layer selected from the group consisting of an emitting layer, a hole injection layer, a hole transport layer, an electron blocking layer, a hole blocking layer, an electron transport layer and an electron injection layer between the first electrode and the second electrode.

* * * * *